(12) United States Patent
Nii

(10) Patent No.: US 6,555,959 B1
(45) Date of Patent: Apr. 29, 2003

(54) MATERIAL FOR LIGHT EMITTING DEVICE, LIGHT EMITTING DEVICE USING THEREOF, AND AMINE COMPOUND

(75) Inventor: Kazumi Nii, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 68 days.

(21) Appl. No.: 09/672,823

(22) Filed: Sep. 29, 2000

(30) Foreign Application Priority Data

Sep. 30, 1999 (JP) ............................................ 11-280205
Jan. 19, 2000 (JP) ........................................ 2000-010775

(51) Int. Cl.$^7$ ......................... A01L 51/30; C01K 11/06; H01J 63/04
(52) U.S. Cl. ...................... 313/506; 313/504; 428/917; 252/301.16; 252/301.21; 252/301.26; 252/301.31; 430/73; 430/74; 564/305; 564/306; 564/426; 564/431; 564/434; 564/442; 564/453; 564/457; 564/458; 564/461; 564/511
(58) Field of Search ........................ 428/917; 313/504, 313/506; 252/301.16, 301.21, 301.26, 301.31; 430/73, 74; 564/305, 306, 426, 431, 434, 442, 453, 457, 458, 461, 511

(56) References Cited

U.S. PATENT DOCUMENTS

| | | | | |
|---|---|---|---|---|
| 3,653,887 A | * | 4/1972 | Merrill .......................... | 430/73 |
| 4,082,721 A | * | 4/1978 | Kok et al. ................. | 106/31.43 |
| 4,092,162 A | * | 5/1978 | Wright et al. .............. | 96/1.5 N |
| 4,111,693 A | * | 9/1978 | Wright et al. .............. | 430/57.2 |
| 4,175,961 A | * | 11/1979 | Wright et al. ............. | 430/58.75 |
| 4,197,120 A | * | 4/1980 | Wright et al. .................. | 430/32 |
| 4,331,751 A | * | 5/1982 | Isaacson et al. .............. | 430/18 |
| 5,814,244 A | * | 9/1998 | Kreuder et al. ......... | 252/301.16 |
| 5,908,581 A | * | 6/1999 | Chen et al. ............ | 252/301.16 |
| 6,143,434 A | * | 11/2000 | Okada ......................... | 313/502 |
| 6,267,913 B1 | * | 7/2001 | Marder et al. ......... | 252/301.17 |
| 6,479,171 B1 | * | 11/2002 | Ishibashi et al. ............. | 428/690 |
| 6,492,557 B1 | * | 12/2002 | Ichimura et al. ............. | 564/434 |
| 6,495,274 B1 | * | 12/2002 | Ishibashi et al. ............. | 428/690 |

FOREIGN PATENT DOCUMENTS

| JP | A-5-179240 | 7/1993 |
|---|---|---|
| JP | A-10-152677 | 6/1998 |

OTHER PUBLICATIONS

Patent Abstract of Japan (05–179240).
Patent Abstract of Japan (10–152677).

* cited by examiner

*Primary Examiner*—Robert Dawson
*Assistant Examiner*—Jeffrey B. Robertson
(74) *Attorney, Agent, or Firm*—Sughrue Mion, PLLC

(57) ABSTRACT

A material for a light emitting device which is a compound represented by the following formula (I):

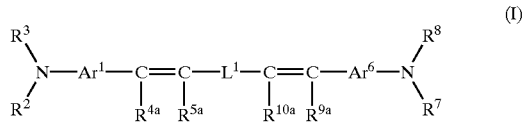

wherein $Ar^1$ and $Ar^6$, which are the same or different, each represents a divalent aryl group or a divalent heterocyclic group; $R^2$, $R^3$, $R^7$ and $R^8$, which are the same or different, each represents an aryl group, a heterocyclic group or an aliphatic hydrocarbon group; $R^{4a}$, $R^{5a}$, $R^{9a}$ and $R^{10a}$, which are the same or different, each represents a hydrogen atom or a monovalent group, and at least one of $R^{4a}$, $R^{5a}$, $R^{9a}$ and $R^{10a}$ represents an electron withdrawing group having a Hammett's $\sigma_p$ value of 0.2 or more; at least two of $Ar^1$, $R^2$, $R^3$, $R^{4a}$, and $R^{5a}$ may be linked to form a ring; at least two of $R^{9a}$, $R^{10a}$, $Ar^6$, $R^7$, and $R^8$ may be linked to form a ring; at least two of $R^{4a}$, $R^{5a}$, $R^{9a}$ and $R^{10a}$ may be linked to form a ring; $L^1$ represents (i) a divalent monocyclic or bicyclic aryl group, or a divalent monocyclic or bicyclic aryl group to which a heterocyclic ring is condensed, (ii) a divalent heterocyclic group, or (iii) a divalent group comprising one of two divalent aryl groups, two divalent heterocyclic groups, and a divalent aryl group and a divalent heterocyclic group, which groups are each connected by a single bond, a vinyl group, a C=X group, a silyl group, an aryl group, a 6-membered aromatic heterocyclic group, a 5-membered aromatic heterocyclic group comprising a carbon atom, a nitrogen atom and an oxygen atom, or the combination of these groups; $L^1$ and at least one of $R^{4a}$ and $R^{5a}$ may be linked to form a ring; $L^1$ and at least one of $R^{9a}$ and $R^{10a}$ may be linked to form a ring; X represents an oxygen atom, a sulfur atom, N—$R^{x1}$ or C$R^{x2}R^{x3}$; and $R^{x1}$, $R^{x2}$ and $R^{x3}$, which are the same or different, each represents a hydrogen atom or a substituent.

8 Claims, No Drawings

MATERIAL FOR LIGHT EMITTING DEVICE, LIGHT EMITTING DEVICE USING THEREOF, AND AMINE COMPOUND

FIELD OF THE INVENTION

The present invention relates to a compound suitable for use for a filter dye, a color conversion filter, a dye for a photographic material, a sensitizing dye, a dye for pulp-dyeing, a laser dye, a fluorescent medicine for a medical diagnosis, a material for a light emitting device (luminescence device), etc., and particularly relates to a light emitting device using thereof.

BACKGROUND OF THE INVENTION

Prospects of an organic light emitting device in which organic materials are used are promising as a solid light emitting (luminescent) type inexpensive and large area full color display device and development has been tried variously. An organic light emitting device in general comprises a light emitting (luminescent) layer and a pair of counter electrodes with the light emitting layer between. When an electric field is impressed between both electrodes, electrons are injected from the cathode and positive holes are injected from the anode, and the electrons and the positive holes are recombined in the light emitting layer. A phenomenon of emitting energy as light when energy level is returned from conduction band to valence band is luminescence.

Organic light emitting devices so far been used require high driving voltage and emission luminance and luminous efficacy are low, but an organic EL device comprising lamination of thin layers containing an organic compound having high fluorescent quantum efficiency capable of emitting light with low voltage of 10 V or lower has been reported (*Applied Physics Letters*, Vol. 51, p. 913 (1987)) and attracting public attention in recent years. According to this technique, high luminance green light emission can be obtained by using a metal chelate complex as the electron-transporting layer, a fluorescent compound as the light emitting layer and an amine compound as the positive hole-transporting layer. Further, when taking into consideration the utilization of an organic light emitting device as a full color display and a light source, it is necessary to get three primary colors or a white color in practical use. A device capable of emitting a desired color by doping a fluorescent dye is reported (*Journal of Applied Physics*, Vol. 65, p. 3610 (1989)). This technique is particularly effective for red emission dyes in which extinction due to concentration is large and the emission of high efficacy is difficult when a fluorescent dye is used alone as the light emitting layer, and high color purity and high luminance have been attained due to the technique. However, when a device doped with a dye is produced by deposition, the operation is complicated and the performance of the device is liable to become uneven because a host material and a trace amount of a fluorescent dye are co-deposited. Therefore, from the viewpoint of the simplification of the producing step and the stability of the performance of a device, the development of light emitting materials of from orange to red capable of high luminance emission and excellent in durability even when a dye is used alone as the light emitting layer has so far been desired.

On the other hand, organic EL devices which have realized high luminance emission are laminated devices formed by vacuum deposition of organic materials, but from the viewpoint of simplification of producing step, process-ability, and realization of large area devices, it is desired to produce devices by a coating system. However, devices produced by a coating system so far been used are inferior to devices produced by a deposition system in the points of emission luminance and luminous efficacy, therefore, the realizations of high luminance and high efficacy luminescence have been left as the problems to be solved. In addition, with devices produced by coating an organic low molecular weight compound dispersed in an organic polymer medium, uniform planar emission for a long period of time is difficult due to the agglomeration of the organic low molecular weight compound.

Further, in recent years, various materials having fluorescence have been used for a filter dye, a color conversion filter, a dye for a photographic material, a sensitizing dye, a dye for pulp-dyeing, a laser dye, a fluorescent medicine for a medical diagnosis, a material for an organic light emitting device, etc., and demand for such materials has been increased. However, fluorescent dyes having high fluorescent strength and capable of long wave emission of from orange to red are less, therefore, the development of a novel material has been desired.

SUMMARY OF THE INVENTION

A first object of the present invention is to provide a material for a light emitting device of orange to red emission capable of emitting light with high luminance and high efficacy, excellent in stability at repeated use, and capable of uniform and planar emission with low voltage driving, and a light emitting device using the same.

A second object of the present invention is to provide a light emitting device showing no unevenness among devices and stable in performance, and a material capable of producing a light emitting device of red emission.

A third object of the present invention is to provide a material for a light emitting device capable of emitting light with high luminance and high efficacy even when a device is produced by coating system, and a light emitting device using the same.

A fourth object of the present invention is to provide a compound having fluorescence of from orange to red with high fluorescent strength.

The above objects of the present invention have been accomplished by the following means.

(1) A material for a light emitting device which is a compound represented by the following formula (I):

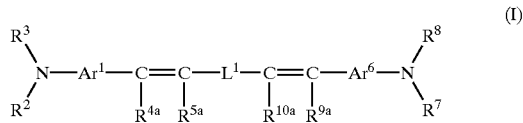

wherein $Ar^1$ and $Ar^6$, which may be the same or different, each represents a divalent aryl group or a divalent heterocyclic group; $R^2$, $R^3$, $R^7$ and $R^8$, which may be the same or different, each represents an aryl group, a heterocyclic group or an aliphatic hydrocarbon group; $R^{4a}$, $R^{5a}$, $R^{9a}$ and $R^{10a}$, which may be the same or different, each represents a hydrogen atom or a monovalent group, and at least one of $R^{4a}$, $R^{5a}$, $R^{9a}$ and $R^{10a}$ represents an electron withdrawing group having a Hammett's $\sigma_p$ value of 0.2 or more; at least two of $Ar^1$, $R^2$, $R^3$, $R^{4a}$, and $R^{5a}$ may be linked to form a ring; at least two of $R^{9a}$, $R^{10a}$, $Ar^6$, $R^7$, and $R^8$ may be linked to form a ring; at least two of $R^{4a}$, $R^{5a}$, $R^{9a}$ and $R^{10a}$ may be linked to form a ring; $L^1$ represents (i) a divalent monocyclic or bicyclic aryl group, or a divalent monocyclic or bicyclic aryl group to which a heterocyclic ring is condensed, (ii) a divalent heterocyclic group, or (iii) a divalent group comprising two divalent aryl groups, two divalent heterocyclic groups, or a divalent aryl group and a divalent heterocyclic group, which groups are each connected by a single bond, a vinyl group, a C=X group, a silyl group, an aryl group, a 6-membered aromatic heterocyclic group, a 5-membered aromatic heterocyclic group having a carbon atom, a nitrogen atom and an oxygen atom as the ring-constitutional atoms, or the combination of these groups; $L^1$ and at least one of $R^{4a}$ and $R^{5a}$ may be linked to form a ring; $L^1$ and at least one of $R^{9a}$ and $R^{10a}$ may be linked to form a ring; X represents an oxygen atom, a sulfur atom, N—$R^{x1}$ or $CR^{x2}R^{x3}$; and $R^{x1}$, $R^{x2}$ and $R^{x3}$, which may be the same or different, each represents a hydrogen atom or a substituent.

(2) The material for a light emitting device as described in the above item (1), wherein the compound represented by formula (I) is a compound represented by the following formula (II):

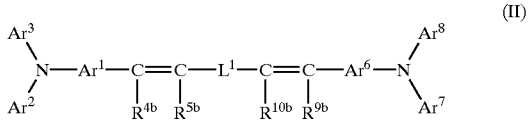

(II)

wherein $Ar^1$, $Ar^6$ and $L^1$ each has the same meaning as in formula (I); $Ar^2$, $Ar^3$, $Ar^7$ and $Ar^8$, which may be the same or different, each represents an aryl group or a heterocyclic group; $R^{4b}$, $R^{5b}$, $R^{9b}$ and $R^{10b}$, which may be the same or different, each represents a hydrogen atom, a heterocyclic group, a perhalogenoalkyl group, a cyano group, an oxycarbonyl group, a carbamoyl group, a sulfonyl group, a sulfamoyl group, or an acyl group, provided that all of $R^{4b}$, $R^{5b}$, $R^{9b}$ and $R^{10b}$ do not represent hydrogen atoms at the same time; at least two of $Ar^1$, $Ar^2$, $Ar^3$, $R^{4b}$ and $R^{5b}$ may be linked to form a ring; at least two of $R^{9b}$, $R^{10b}$, $Ar^6$, $Ar^7$, and $Ar^8$ may be linked to form a ring; at least two of $R^{4b}$, $R^{5b}$, $R^{9b}$ and $R^{10}$ may be linked to form a ring; $L^1$ and at least one of $R^{4b}$ and $R^{5b}$ may be linked to form a ring; and $L^1$ and at least one of $R^{9b}$ and $R^{10b}$ may be linked to form a ring.

(3) The material for a light emitting device as described in the above item (2), wherein the compound represented by formula (II) is a compound represented by the following formula (III):

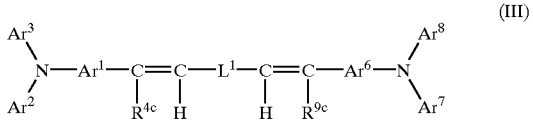

(III)

wherein $Ar^1$, $Ar^2$, $Ar^3$, $Ar^6$, $Ar^7$, $Ar^8$ and $L^1$ each has the same meaning as in formula (II); at least two of $Ar^1$, $Ar^2$ and $Ar^3$ may be linked to form a ring; at least two of $Ar^6$, $Ar^7$ and $Ar^8$ may be linked to form a ring; and $R^{4c}$ and $R^{9c}$, which may be the same or different, each represents a heterocyclic group, a perhalogenoalkyl group, a cyano group, an oxycarbonyl group, a carbamoyl group, a sulfonyl group, a sulfamoyl group, or an acyl group.

(4) An amine compound represented by the following formula (IV):

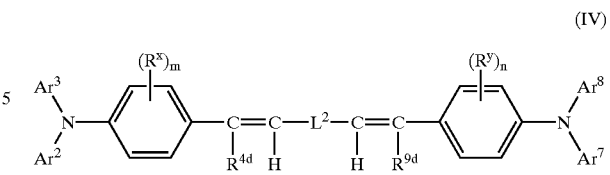

(IV)

wherein $Ar^2$, $Ar^3$, $Ar^7$ and $Ar^8$, which maybe the same or different, each represents an aryl group or a heterocyclic group; $R^x$ and $R^y$ each represents a substituent; m and n each represents an integer of 0 to 4, when m and n each represents 2, 3 or 4, a plurality of $R^x$ and $R^y$ may be the same with or different from each other; at least two of $Ar^2$, $Ar^3$ and $R^x$ may be linked to form a ring; at least two of $Ar^7$, $Ar^8$ and $R^y$ may be linked to form a ring; $R^{4d}$ and $R^{9d}$, which may be the same or different, each represents a heterocyclic group, a cyano group, an oxycarbonyl group, a sulfonyl group, or an acyl group; and $L^2$ represents (i) a divalent monocyclic orbicyclic aryl group, or a divalent monocyclic or bicyclic aryl group to which a heterocyclic ring is condensed, (ii) a divalent heterocyclic group, or (iii) a divalent group comprising two divalent aryl groups, two divalent heterocyclic groups, or a divalent aryl group and a divalent heterocyclic group, which groups are each connected by a single bond, a vinyl group, an aryl group, a 6-membered aromatic heterocyclic group, a 5-membered aromatic heterocyclic group having a carbon atom, a nitrogen atom and an oxygen atom as the ring-constitutional atoms, or the combination of these groups.

(5) A light emitting device comprising a pair of electrodes and at least one organic thin layer between the electrodes, wherein the light emitting device comprises at least one compound represented by formula (I), (II), (III) or (IV) as described in the above item (1), (2), (3) or (4).

(6) A light emitting device comprising a pair of electrodes and at least one organic thin layer between the electrodes, wherein at least one layer is a layer containing at least one compound represented by formula (I), (II), (III) or (IV) as described in the above item (1), (2), (3) or (4) dispersed in a polymer.

DETAILED DESCRIPTION OF THE INVENTION

In the first place, a compound represented by formula (I) will be described in detail below.

In formula (I), $Ar^1$ and $Ar^6$, which may be the same or different, each represents a divalent aryl group, or a divalent heterocyclic group. The divalent aryl group represented by $Ar^1$ and $Ar^6$ is preferably a monocyclic or bicyclic aryl group having from 6 to 30 carbon atoms (e.g., phenyl, naphthyl, biphenyl, fluorenyl), more preferably a phenyl or naphthyl group having from 6 to 20 carbon atoms, and still more preferably a phenyl or naphthyl group having from 6 to 14 carbon atoms.

The divalent heterocyclic group represented by $Ar^1$ and $Ar^6$ is a 3- to 10-membered saturated or unsaturated heterocyclic ring containing at least one N, O or S atom. The heterocyclic ring may be a monocyclic ring or may further form a condensed ring with other ring.

The heterocyclic group is preferably a 5- or 6-membered aromatic heterocyclic group, more preferably a 5- or 6-membered aromatic heterocyclic group containing a nitrogen atom, an oxygen atom or a sulfur atom, and still more preferably a 5- or 6-membered aromatic heterocyclic group containing one or two of a nitrogen atom and a sulfur atom.

Specific examples of the heterocyclic rings include, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene, preferred examples include thiophene, pyridine and quinoline.

The aryl group and the heterocyclic group represented by $Ar^1$ and $Ar^6$ may have substituents, and examples of the substituents include, for example, an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl, allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, naphthyl), an amino group (preferably an amino group having from 0 to 20, more preferably from 0 to 10, and particularly preferably from 0 to 6, carbon atoms, e.g., amino, methylamino, dimethylamino, diethylamino, dibenzylamino), an alkoxyl group (preferably an alkoxyl group having from 1 to 20, more preferably from 1 to 12, and particularly preferably from 1 to 8, carbon atoms, e.g., methoxy, ethoxy, butoxy), an aryloxy group (preferably an aryloxy group having from 6 to 20, more preferably from 6 to 16, and particularly preferably from 6 to 12, carbon atoms, e.g., phenyloxy, 2-naphthyloxy), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e.g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), an acyloxy group (preferably an acyloxy group having from 2 to 20, more preferably from 2 to 16, and particularly preferably from 2 to 10, carbon atoms, e.g., acetoxy, benzoyloxy), an acylamino group (preferably an acylamino group having from 2 to 20, more preferably from 2 to 16, and particularly preferably from 2 to 10, carbon atoms, e.g., acetylamino, benzoylamino), an alkoxycarbonylamino group (preferably an alkoxycarbonylamino group having from 2 to 20, more preferably from 2 to 16, and particularly preferably from 2 to 12, carbon atoms, e.g., methoxycarbonylamino), an aryloxycarbonylamino group (preferably an aryloxy-carbonylamino group having from 7 to 20, more preferably from 7 to 16, and particularly preferably from 7 to 12, carbon atoms, e.g., phenyloxycarbonylamino), a sulfonylamino group (preferably a sulfonylamino group having from 1 to 20, more preferably from 1 to 16, and particularly preferably from 1 to 12, carbon atoms, e.g., methanesulfonylamino, benzene-sulfonylamino), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenyl-sulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenyl-carbamoyl), an alkylthio group (preferably an alkylthio group having from 1 to 20, more preferably from 1 to 16, and particularly preferably from 1 to 12, carbon atoms, e.g., methylthio, ethylthio), an arylthio group (preferably an arylthio group having from 6 to 20, more preferably from 6 to 16, and particularly preferably from 6 to 12, carbon atoms, e.g., phenylthio), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), a ureido group (preferably a ureido group having from 1 to 20, more preferably from 1 to 16, and particularly preferably from 1 to 12, carbon atoms, e.g., ureido, methylureido, phenylureido), a phosphoric acid amido group (preferably a phosphoric acid amido group having from 1 to 20, more preferably from 1 to 16, and particularly preferably from 1 to 12, carbon atoms, e.g., diethylphosphoric acid amido, phenylphosphoric acid amido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, a heterocyclic group (preferably a heterocyclic group having from 1 to 20, and more preferably from 1 to 12, carbon atoms; as hetero atoms, e.g., nitrogen, oxygen, sulfur, and specifically, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene can be exemplified), and a silyl group (preferably a silyl group having from 3 to 40, more preferably from 3 to 30, and particularly preferably from 3 to 24, carbon atoms, e.g., trimethylsilyl, triphenylsilyl). These substituents may further be substituted. When there are two or more substituents, they may be the same or different. Substituents may be linked to each other to form a ring, if possible.

Preferred examples of the substituents include an alkyl group, analkenyl group, anaralkyl group, anaryl group, an alkoxyl group, an amino group, an acyl group, an alkoxycarbonyl group, an aryloxycarbonyl group, a carbonylamino group, a sulfonylamino group, a sulfamoyl group, a carbamoyl group, a hydroxyl group, and a heterocyclic group, more preferred examples include an alkyl group, an alkenyl group, an aralkyl group, an aryl group, an alkoxyl group, an amino group, anacylamino group, analkoxycarbonylamino group, an aryloxycarbonylamino group, a sulfonylamino group, and a heterocyclic group, and still more preferred examples include an alkyl group, an alkenyl group, an aryl group, an alkoxyl group, and a substituted amino group.

Here, the substituted amino group is a group represented by —$Nr_a(R_b)$, wherein $R_a$ and $R_b$ may be the same or different, and specifically represents an alkyl group, an alkenyl group, an aralkyl group, an aryl group, or a heterocyclic group. As these alkyl, alkenyl, aryl and heterocyclic groups, the same groups described as the substituents of $Ar^1$ can be exemplified. The aralkyl is an aralkyl group having from 7 to 20, more preferably from 7 to 16, and particularly preferably from 7 to 10, carbon atoms, e.g., a benzyl group and a phenethyl group can be exemplified.

$R^2$, $R^3$, $R^7$ and $R^8$, which may be the same or different, each represents an aryl group, a heterocyclic group or an aliphatic hydrocarbon group.

The aryl group represented by $R^2$, $R^3$, $R^7$ and $R^8$ is preferably a monocyclic, bicyclic, tricyclic or tetracyclic aryl group having from 6 to 26 carbon atoms (e.g., phenyl, naphthyl, anthryl, phenanthryl, pyrenyl, indenyl), more preferably phenyl, naphthyl, anthryl, or phenanthryl each having from 6 to 20 carbon atoms, and still more preferably phenyl, naphthyl or anthryl each having from 6 to 14 carbon atoms.

The heterocyclic group represented by $R^2$, $R^3$, $R^7$ and $R^8$ is a 3- to 10-membered saturated or unsaturated heterocyclic ring containing at least one N, O or S atom. The heterocyclic ring may be a monocyclic ring or may further form a condensed ring with other ring.

The heterocyclic group is preferably a 5- or 6-membered aromatic heterocyclic group, more preferably a 5- or 6-membered aromatic heterocyclic group containing a nitrogen atom, an oxygen atom or a sulfur atom, and still more preferably a 5- or 6-membered aromatic heterocyclic group containing one or two of a nitrogen atom and a sulfur atom. Specific examples of the heterocyclic rings include, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene, preferred examples include thiophene, pyridine and quinoline.

The aliphatic hydrocarbon group represented by $R^2$, $R^3$, $R^7$ and $R^8$ may be straight chain, branched or cyclic, e.g., an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl, allyl, 2-butenyl, 3-pentenyl), or an alkynyl group (preferably an alkynyl group having from 2 to 20, more preferably from 2 to 12, and particularly preferably from 2 to 8, carbon atoms, e.g., propargyl, 3-pentynyl). The aliphatic hydrocarbon group is preferably an alkyl group.

The aryl group, the heterocyclic group and the aliphatic hydrocarbon group represented by $R^2$, $R^3$, $R^7$ and $R^8$ may have substituents, and may further form a condensed ring. As the substituents, those described above as the substituents of $Ar^1$ and $Ar^6$ can be applied to.

Two or three of $Ar^1$, $R^2$ and $R^3$ may be linked to form a ring, and the ring to be formed is preferably a 5 to 7-membered ring. At least two of $Ar^6$, $R^7$ and $R^8$ may also be linked to form a ring, and the ring to be formed is preferably a 5 to 7-membered ring.

$R^{4a}$, $R^{5a}$, $R^{9a}$ and $R^{10a}$, which may be the same or different, each represents a hydrogen atom or a substituent, and as the substituents, e.g., those described above as the substituents of $Ar^1$ and $Ar^6$ can be applied to. At least one of $R^{4a}$, $R^{5a}$, $R^{9a}$ and $R^{10a}$ represents an electron withdrawing group having a Hammett's $\sigma_p$ value of 0.2 or more. As the electron withdrawing group having a Hammett's $\sigma_p$ value of 0.2 or more, e.g., a halogen atom, a perhalogenoalkyl group (e.g., a perfluoroalkyl group, a perchloroalkyl group, a perbromoalkyl group), a cyano group, a formyl group, a carboxyl group, a carbamoyl group, a sulfonylmethyl group, an acyl group, an oxycarbonyl group (preferably an oxycarbonyl group substituted with an aliphatic hydrocarbon group, an aryl group or a heterocyclic group; the aliphatic hydrocarbon group, the aryl group and the heterocyclic group have the same meaning as those described in $R^2$), a pentahalophenyl group, a carbonyloxy group, a sulfonyloxy group, a sulfonyl group, a sulfinyl group, a heterocyclic group and a sulfamoyl group can be exemplified. Preferred examples are a heterocyclic group, a perhalogenoalkyl group, a cyano group, an oxycarbonyl group, a carbamoyl group, a sulfonyl group, a sulfamoyl group and an acyl group, and particularly preferred examples are benzoxazole, benzothiazole, benzimidazole, a cyano group, an oxycarbonyl group, a sulfonyl group, a sulfamoyl group and an acyl group.

At least two of $Ar^1$, $R^2$, $R^3$, $R^{4a}$, and $R^{5a}$ may be linked to form a ring. At least two of $R^{9a}$, $R^{10a}$, $Ar^6$, $R^7$, and $R^8$ may be linked to form a ring. At least two of $R^{4a}$, $R^{5a}$, $R^{9a}$ and $R^{10a}$ may be linked to form a ring.

$L^1$ and at least one of $R^{4a}$ and $R^{5a}$ may be linked to form a ring. $L^1$ and at least one of $R^{9a}$ and $R^{10a}$ may be linked to form a ring.

$L^1$ represents (i) a divalent monocyclic or bicyclic aryl group, or a divalent monocyclic or bicyclic aryl group to which a heterocyclic ring is condensed, (ii) a divalent heterocyclic group, or (iii) a divalent group comprising two divalent aryl groups, two divalent heterocyclic groups, or a divalent aryl group and a divalent heterocyclic group, which groups are each connected by a single bond, a vinyl group, a C=X group, a silyl group, an aryl group, a 6-membered aromatic heterocyclic group, a 5-membered aromatic heterocyclic group having a carbon atom, a nitrogen atom and an oxygen atom as the ring-constitutional atoms, or the combination of these groups. Here, the divalent aryl group and the divalent heterocyclic group each has the same meaning as the divalent aryl group and the divalent heterocyclic group as defined in $Ar^1$ and $Ar^6$, and they may further contain a heterocyclic ring and may be condensed to form a 2- to 5-membered ring. The divalent aryl group is preferably a divalent monocyclic or bicyclic aryl group, or a divalent group a divalent monocyclic or bicyclic aryl group to which a heterocyclic ring is condensed. More preferred examples of the heterocyclic groups include thiophene, pyrrole, imidazole, pyrazole, pyridine, pyrazine, pyridazine, triazole, triazine, indole, indazole, thiazole, thiadiazole, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, and benzotriazole. When $L^1$ represents a group comprising two divalent aryl groups, two divalent heterocyclic groups, or a divalent aryl group and a divalent heterocyclic group each connected by an aromatic heterocyclic group, the aromatic heterocyclic group is preferably a 6-membered aromatic heterocyclic group. X represents an oxygen atom, a sulfur atom, N—$R^{x1}$ or $CR^{x2}R^{x3}$; and $R^{x1}$, $R^{x2}$ and $R^{x3}$, which may be the same or different, each represents a hydrogen atom or a substituent. X preferably represents an oxygen atom, a sulfur atom, or $CR^{x2}R^{x3}$. The substituents are the same as those described above as the substituents of $Ar^1$ and $Ar^6$. $R^{x1}$ preferably represents a hydrogen atom, an alkyl group, an aryl group, or a heterocyclic group, and $R^{x2}$ and $R^{x3}$ each preferably represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{x2}$ and $R^{x3}$ do not represent hydrogen atoms at the same time. More preferably, the alkyl, aryl or heterocyclic group represented by $R^{x2}$, $R^{x2}$ and $R^{x3}$ each has the same meaning as the alkyl, aryl or heterocyclic group described above as the substituents represented by $Ar^1$ and $Ar^6$. The alkyl group represented by $R^{x2}$ and $R^{x3}$ is preferably a perfluoroalkyl group, i.e., a straight chain, branched or cyclic alkyl group having fluorine as a substituent (preferably having from 1 to 30, more preferably from 1 to 20, and still more preferably from 1 to 12 carbon atoms, e.g., a trifluoromethyl group, a pentafluoromethyl group).

The oxycarbonyl group, carbamoyl group, sulfonyl group, sulfamoyl group, or acyl group represented by $R^{x2}$ and $R^{x3}$ is preferably an oxycarbonyl group, a carbamoyl group, a sulfonyl group, a sulfamoyl group, or an acyl group substituted with an aliphatic hydrocarbon group, an aryl group or a heterocyclic group, and each group has the same meaning as the oxycarbonyl group, carbamoyl group, sulfonyl group, sulfamoyl group, or acyl group represented by $R^4$, $R^{5a}$, $R^{9a}$ and $R^{10a}$, and the preferred range is also the same.

$R^{x2}$ and $R^{x3}$ may be linked to form a ring.

As the examples of $L^1$, the following compounds can be exemplified, for instance.

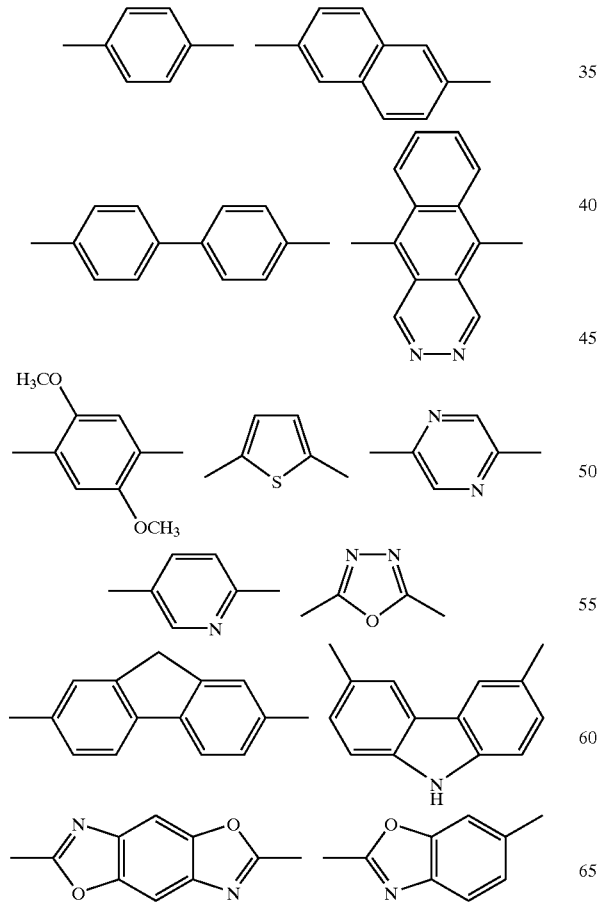

-continued

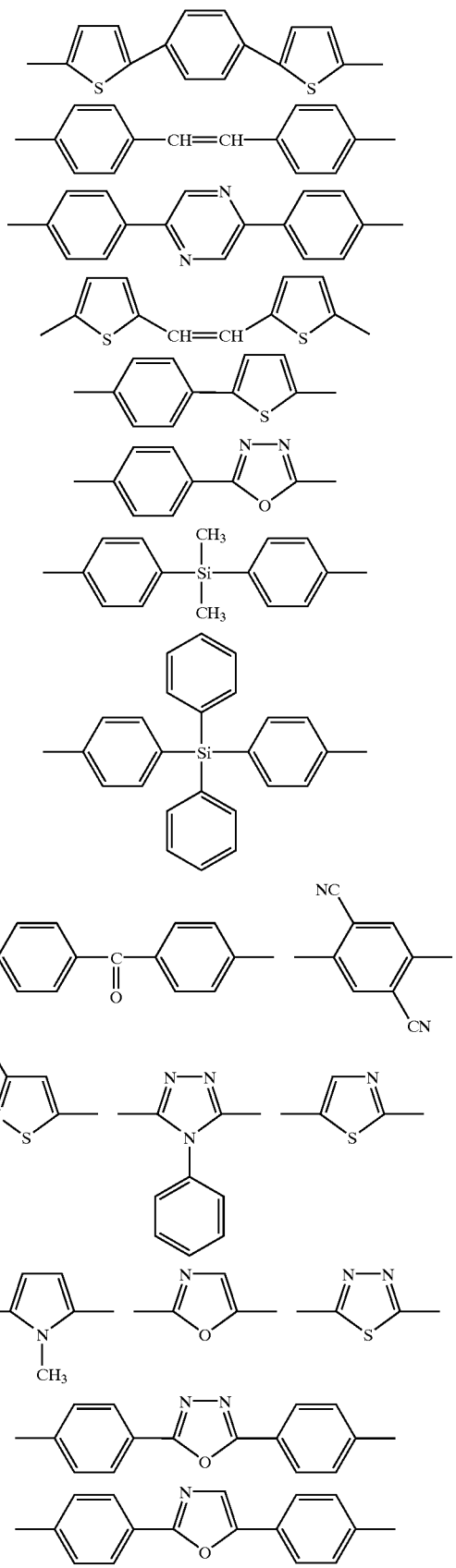

A compound represented by formula (II) will be described in detail below.

$Ar^1$, $Ar^6$ and $L^1$ each has the same meaning as in formula (I) and each preferred range is also the same. $Ar^2$, $Ar^3$, $Ar^7$ and $Ar^8$, which may be the same or different, each represents an aryl group or a heterocyclic group, and has the same meaning as the aryl group or the heterocyclic group represented by $R^2$, $R^3$, $R^7$ and $R^8$ in formula (I), and each preferred range is also the same. $R^{4b}$, $R^{5b}$, $R^{9b}$ and $R^{10b}$ beach represents a hydrogen atom, a heterocyclic group, a perhalogenoalkyl group, a cyano group, an oxycarbonyl group, a carbamoyl group, a sulfonyl group, a sulfamoyl group, or an acyl group, provided that all of $R^{4b}$, $R^{5b}$, $R^{9b}$ and $R^{10b}$ do not represent hydrogen atoms at the same time.

Preferably, the heterocyclic group represented by $R^{4b}$, $R^{5b}$, $R^{9b}$ and $R^{10b}$ has the same meaning as the heterocyclic group represented by $R^2$, $R^3$, $R^7$ and $R^8$ The heterocyclic group represented by $R^{4b}$, $R^{5b}$, $R^{9b}$ and $R^{10b}$ is more preferably benzoxazole, benzothiazole or benzimidazole.

The oxycarbonyl group, carbamoyl group, sulfonyl group, sulfamoyl group, or acyl group represented by $R^{4b}$, $R^{5b}$, $R^{9b}$ and $R^{10b}$ is preferably an oxycarbonyl group, a carbamoyl group, a sulfonyl group, a sulfamoyl group, or an acyl group substituted with an aliphatic hydrocarbon group, an aryl group or a heterocyclic group.

In this case, the aliphatic hydrocarbon group has the same meaning as the aliphatic hydrocarbon group represented by $R^2$, $R^3$, $R^7$ and $R^8$, preferably the aliphatic hydrocarbon group is an alkyl group or an alkenyl group, and more preferably a methyl group, an ethyl group, a propyl group, a butyl group, a trifluoromethyl group, or an allyl group.

The aryl group preferably has the same meaning as the aryl group represented by $R^2$, $R^3$, $R^7$ and $R^8$. The heterocyclic group preferably has the same meaning as the heterocyclic group represented by $R^2$, $R^3$, $R^7$ and $R^8$. They may be monocyclic or may form a condensed ring with other rings.

$R^{4b}$, $R^{4b}$, $R^{9b}$ and $R^{10b}$ each more preferably represents a hydrogen atom, a heterocyclic group, a perhalogenoalkyl group, a cyano group, an oxycarbonyl group, a sulfonyl group, or an acyl group.

A compound represented by formula (III) will be described in detail below.

$Ar^1$, $Ar^2$, $Ar^3$, $Ar^6$, $Ar^7$, $Ar^8$ and $L^1$ each has the same meaning as in formula (II) and each preferred range is also the same. $R^{4c}$ and $R^{9c}$, which may be the same or different, each represents a heterocyclic group, a perhalogenoalkyl group, a cyano group, an oxycarbonyl group, a carbamoyl group, a sulfonyl group, a sulfamoyl group, or an acyl group, and each group has the same meaning as each group represented by $R^{4b}$, $R^{5b}$, $R^{9b}$ and $R^{10b}$ and the preferred range of each group is also the same.

A compound represented by formula (IV) will be described in detail below.

$Ar^2$, $Ar^3$, $Ar^7$ and $Ar^8$ each has the same meaning as in formula (III) and each preferred range is also the same. $R^x$ and $R^y$ each represents a substituent (those exemplified as the substituents of $Ar^1$ can be applied to). m and n each represents an integer of 0 to 4, when m and n each represents 2, 3 or 4, a plurality of $R^x$ and $R^y$ may be the same with or different from each other. At least two of $Ar^2$, $Ar^3$ and $R^x$ may be formed to form a ring, and/or at least two of $Ar^7$, $Ar^8$ and $R^y$ may be linked to form a ring, and the ring to be formed is preferably a 5- to 7-membered ring. $R^{4d}$ and $R^{9d}$, which may be the same or different, each represents a heterocyclic group, a cyano group, an oxycarbonyl group, a sulfonyl group, or an acyl group, and each group has the same meaning as each group represented by $R^{4b}$, $R^{5b}$, $R^{9b}$ and $R^{10b}$ in formula (II) and the preferred range of each group is also the same. $L^2$ represents (i) a divalent monocyclic or bicyclic aryl group, or a divalent monocyclic or bicyclic aryl group to which a heterocyclic ring is condensed, (ii) a divalent heterocyclic group, or (iii) a divalent group comprising two divalent aryl groups, two divalent heterocyclic groups, or a divalent aryl group and a divalent heterocyclic group, which groups are each connected by a single bond, a vinyl group, an aryl group, a 6-membered aromatic heterocyclic group, a 5-membered aromatic heterocyclic group having a carbon atom, a nitrogen atom and an oxygen atom, or the combination of these groups. The aryl group or the heterocyclic group represented by $L^2$ each preferably has the same meaning as the aryl group or the heterocyclic group represented $Ar^1$ and $Ar^6$ in formula (I). More preferably $L^2$ represents a monocyclic, bicyclic or tricyclic aryl group, a thiophene ring, a pyrrole ring, an imidazole ring, a pyrazole ring, a pyridine ring, a pyrazine ring, a pyridazine ring, a triazine ring, an oxazole ring, an oxadiazole ring, a thiazole ring, a thiadiazole ring, or a bicyclic or tricyclic heterocyclic group comprising any of these groups condensed with a benzene ring.

m and n each preferably represents 0.

$L^2$ particularly preferably represents a monocyclic or condensed bicyclic or tricyclic aryl group or heterocyclic group.

The compounds represented by formulae (I) to (IV) may be low molecular weight compounds, may be high molecular weight compounds (preferably having a weight average molecular weight of from 1,000 to 5,000,000, more preferably from 5,000 to 2,000,000, and particularly preferably from 10,000 to 1,000,000) having the residual monomers of the compounds represented by formulae (I) to (IV) bonded to the polymer main chains, or may be high molecular weight compounds (preferably having a weight average molecular weight of from 1,000 to 5,000,000, more preferably from 5,000 to 2,000,000, and particularly preferably from 10,000 to 1,000,000) having the skeletons of the compounds represented by formulae (I) to (IV) at the main chains. The high molecular weight compounds may be homopolymers or copolymers with other monomers.

The compounds represented by formulae (I) to (IV) are preferably low molecular weight compounds. Further, formulae (I) to (IV) take limiting structures for convenience sake but the compounds may be tautomers thereof.

With respect to the compound represented by formula (I), preferred combinations of the substituents will be described below. $Ar^1$ and $Ar^6$ each represents a divalent monocyclic or bicyclic aryl group having from 6 to 20 carbon atoms, or a divalent 5- or 6-membered aromatic heterocyclic group containing a nitrogen atom, an oxygen atom or a sulfur atom and having from 1 to 20 carbon atoms. $R^2$, $R^3$, $R^7$ and $R^8$, which may be the same or different, each represents a monocyclic, bicyclic, tricyclic or tetracyclic aryl group having from 6 to 30 carbon atoms, a 5- or 6-membered aromatic heterocyclic group containing a nitrogen atom, an oxygen atom or a sulfur atom and having from 1 to 20 carbon atoms, or an alkyl group having from 1 to 20 carbon atoms. $Ar^1$, $Ar^6$, $R^2$, $R^3$, $R^7$ and $R^8$ each may have a substituent. Examples of the substituents include an alkyl group, an alkenyl group, an aralkyl group, an aryl group, an alkoxyl group, an amino group, an acyl group, an alkoxycarbonyl group, an aryloxycarbonyl group, an acylamino group, an alkoxycarbonylamino group, an aryloxycarbonylamino group, a sulfonylamino group, a sulfamoyl group, a carbamoyl group, a hydroxyl group, and a heterocyclic group, and these groups may further be substituted. At least two of $Ar^1$, $R^2$ and $R^3$ may be linked to form a ring, and/or at least two of $Ar^6$, $R^7$ and $R^8$ may be linked to form a ring, and the ring to be formed is preferably a 5- to 7-membered ring.

$R^{4a}$, $R^{5a}$, $R^{9a}$ and $R^{10a}$, which may be the same or different, each represents a hydrogen atom or a monovalent group, and at least one of $R^{4a}$, $R^{5a}$, $R^{9a}$ and $R^{10a}$ represents an electron withdrawing group having a Hammett's $\sigma_p$ value of 0.2 or more. Examples of the substituents (monovalent groups) include an alkyl group, an alkenyl group, an aralkyl group, an aryl group, an alkoxyl group, an amino group, an acyl group, an oxycarbonyl group, a carbonylamino group, a sulfonylamino group, a sulfonyl group, a sulfamoyl group, a carbamoyl group, a cyano group and a heterocyclic group. At least two of $Ar^1$, $R^2$, $R^3$, $R^{4a}$, and $R^{5a}$ may be linked to form a ring. At least two of $R^{9a}$, $R^{10a}$, $Ar^6$, $R^7$, and $R^8$ may be linked to form a ring. At least two of $R^{4a}$, $R^{5a}$, $R^{9a}$ and $R^{10a}$ may be linked to form a ring.

$L^1$ represents (i) a divalent monocyclic or bicyclic aryl group, or a divalent monocyclic or bicyclic aryl group to which a heterocyclic ring is condensed, (ii) a divalent heterocyclic group, or (iii) a divalent group comprising two divalent aryl groups, two divalent heterocyclic groups, or a divalent aryl group and a divalent heterocyclic group, which groups are each connected by a single bond, a vinyl group, a C=X group, a silyl group, an aryl group, a 6-membered aromatic heterocyclic group, a 5-membered aromatic heterocyclic group having a carbon atom, a nitrogen atom and an oxygen atom, or the combination of these groups. Here, the divalent aryl group or the divalent heterocyclic group is a divalent monocyclic or bicyclic aryl group having from 6 to 20 carbon atoms, or a divalent 5- or 6-membered aromatic heterocyclic group containing a nitrogen atom, an oxygen atom or a sulfur atom and having from 1 to 20 carbon atoms. The heterocyclic group and a condensed ring may be further condensed to formed a 2- to 5-membered ring. More preferred examples of the heterocyclic groups include thiophene, pyrrole, imidazole, pyrazole, pyridine, pyrazine, pyridazine, triazole, triazine, indole, indazole, thiazole, thiadiazole, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, and benzotriazole. X represents an oxygen atom, a sulfur atom, N—$R^{x1}$ or $CR^{x2}R^{x3}$ and $R^{x1}$, $R^{x2}$ and $R^{x3}$, which may be the same or different, each represents a hydrogen atom or a substituent. X more preferably represents an oxygen atom, a sulfur atom, or $CR^{x2}R^{x3}$. $R^{x1}$ preferably represents a hydrogen atom, analkyl group, an aryl group, or a heterocyclic group, and $R^{x2}$ and $R^{x3}$ each preferably represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{x2}$ and $R^{x3}$ do not represent hydrogen atoms at the same time. More preferably, the alkyl, aryl or heterocyclic group represented by $R^{x1}$, $R^{x2}$ and $R^{x3}$ each has the same meaning as the alkyl, aryl or heterocyclic group described above as the substituents represented by $Ar^1$ and $Ar^6$.

The alkyl group represented by $R^{x2}$ and $R^{x3}$ is preferably a perfluoroalkyl group, i.e., a straight chain, branched or cyclic alkyl group having fluorine as a substituent (preferably having from 1 to 30, more preferably from 1 to 20, and still more preferably from 1 to 12 carbon atoms, e.g., a trifluoromethyl group, a pentafluoromethyl group).

The oxycarbonyl group, carbamoyl group, sulfonyl group, sulfamoyl group, or acyl group represented by $R^{x2}$ and $R^{x3}$ is preferably an oxycarbonyl group, a carbamoyl group, a sulfonyl group, a sulfamoyl group, or an acyl group substituted with an aliphatic hydrocarbon group, an aryl group or a heterocyclic group, and each group has the same meaning as the oxycarbonyl group, carbamoyl group, sulfonyl group, sulfamoyl group, or acyl group represented by $R^{4a}$, $R^{5a}$, $R^{9a}$ and $R^{10a}$.

The more preferred combination of the substituents of the compound represented by formula (I) is represented by formula (II).

$Ar^1$, $Ar^6$ and $L^1$ each has the same meaning as the combination in formula (I). $Ar^2$, $Ar^3$, $Ar^7$ and $Ar^8$ each preferably represents an aryl group having from 6 to 26 carbon atoms e.g., a phenyl group, a naphthyl group, an anthryl group, a phenanthryl group, or a pyrenyl group, or a 5- or 6-membered aromatic heterocyclic group containing a nitrogen atom, an oxygen atom or a sulfur atom and having from 1 to 20 carbon atoms, and more preferably a 5- or 6-membered aromatic heterocyclic group containing one or two sulfur atoms. $R^{4b}$, $R^{5b}$, $R^{9b}$ and $R^{10b}$, which may be the same or different, each represents a hydrogen atom, a heterocyclic group, a perhalogenoalkyl group, a cyano group, an oxycarbonyl group, a carbamoyl group, a sulfonyl group, a sulfamoyl group, or an acyl group, provided that all of $R^{4b}$, $R^{5b}$, $R^{9b}$ and $R^{10b}$ do not represent hydrogen atoms at the same time.

The heterocyclic group represented by $R^{4b}$, $R^{5b}$, $R^{9b}$ and $R^{10b}$ is a 5- or 6-membered aromatic heterocyclic group containing a nitrogen atom, an oxygen atom or a sulfur atom and having from 1 to 20 carbon atoms. The oxycarbonyl group, carbamoyl group, sulfonyl group, sulfamoyl group, or acyl group represented by $R^{4b}$, $R^{5b}$, $R^{9b}$ and $R^{10b}$ is preferably an oxycarbonyl group, a carbamoyl group, a sulfonyl group, a sulfamoyl group, or an acyl group substituted with an aliphatic hydrocarbon group, an aryl group or a heterocyclic group.

In this case, the aliphatic hydrocarbon group has the same meaning as the aliphatic hydrocarbon group represented by $R^2$, $R^3$, $R^7$ and $R^8$, preferably the aliphatic hydrocarbon group is an alkyl group or an alkenyl group, and more preferably a methyl group, an ethyl group, a propyl group, a butyl group, a trifluoromethyl group, or an allyl group.

The aryl group preferably has the same meaning as the aryl group represented by $R^2$, $R^3$, $R^7$ and $R^8$ The heterocyclic group preferably has the same meaning as the heterocyclic group represented by $R^2$, $R^3$, $R^7$ and $R^8$. They may be monocyclic or may form a condensed ring with other rings.

The more preferred combination of the substituents of the compound represented by formula (II) is represented by formula (III). $Ar^1$, $Ar^2$, $Ar^3$, $Ar^6$, $Ar^7$, $Ar^8$ and $L^1$ each has the same meaning as the combination in formula (II). $R^{4c}$ and $R^{9c}$, which may be the same or different, each represents a heterocyclic group, a perhalogenoalkyl group, a cyano group, an oxycarbonyl group, a carbamoyl group, a sulfonyl group, a sulfamoyl group, or an acyl group.

The more preferred combination of the substituents of the compound represented by formula (III) is represented by formula (IV). $Ar^2$, $Ar^3$, $Ar^7$ and $Ar^8$ each has the same meaning as the combination in formula (III). $R^{4d}$ and $R^{9d}$, which may be the same or different, each represents a heterocyclic group, a cyano group, an oxycarbonyl group, a sulfonyl group, or an acyl group. $L^2$ represents (i) a divalent monocyclic or bicyclic aryl group, or a divalent monocyclic orbicyclic aryl group to which a heterocyclic ring is condensed, (ii) a divalent heterocyclic group, or (iii) a divalent group comprising two divalent aryl groups, two divalent heterocyclic groups, or a divalent aryl group and a divalent heterocyclic group, which groups are each connected by a single bond, a vinyl group, an aryl group, a 6-membered aromatic heterocyclic group, a 5-membered aromatic heterocyclic group having a carbon atom, a nitrogen atom and an oxygen atom, or the combination of these groups. The aryl group or the heterocyclic group represented by $L^2$ each preferably has the same meaning as the aryl group or the heterocyclic group represented $Ar^1$ and $Ar^6$ in formula (I). More preferably, $L^2$ represents a monocyclic, bicyclic or tricyclic aryl group, a thiophene ring, a pyrrole ring, an imidazole ring, a pyrazole ring, a pyridine ring, a pyrazine ring, a pyridazine ring, a triazine ring, an oxazole ring, an oxadiazole ring, a thiazole ring, a thiadiazole ring, or a bicyclic or tricyclic heterocyclic group comprising any of these groups condensed with a benzene ring. $L^2$ particularly preferably represents a monocyclic or condensed bicyclic or tricyclic aryl group or heterocyclic group. m and n each represents 0.

The specific examples of the compounds represented by formula (I) are shown below but it should not be construed as the present invention is limited thereto.

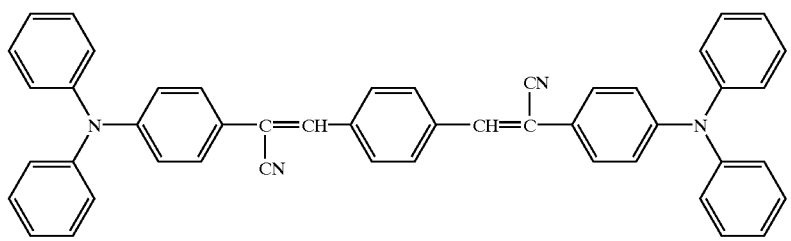

D-1

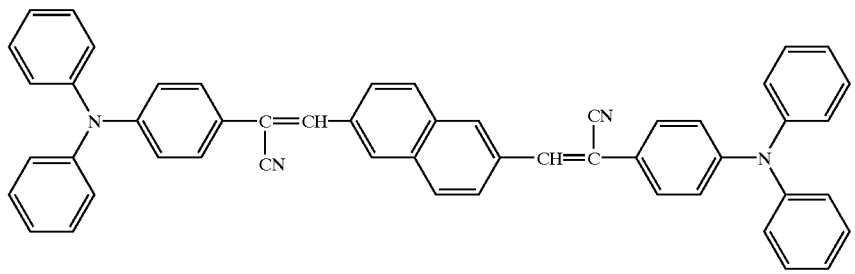

D-2

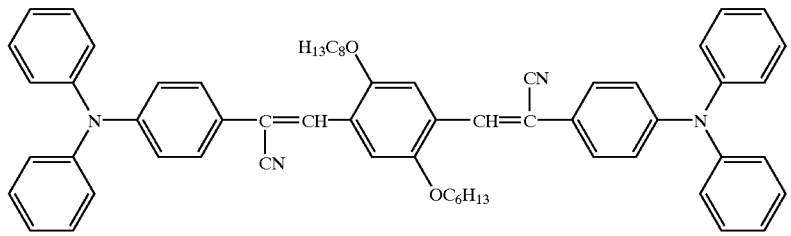

D-3

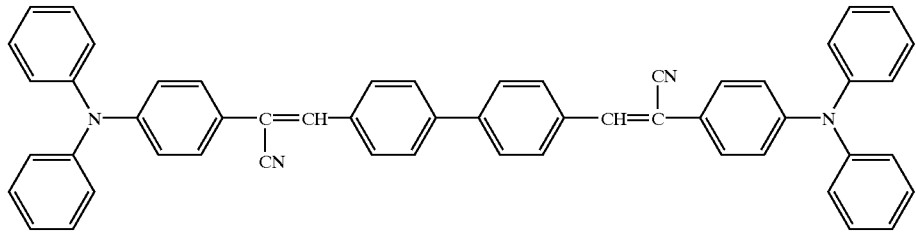

D-4

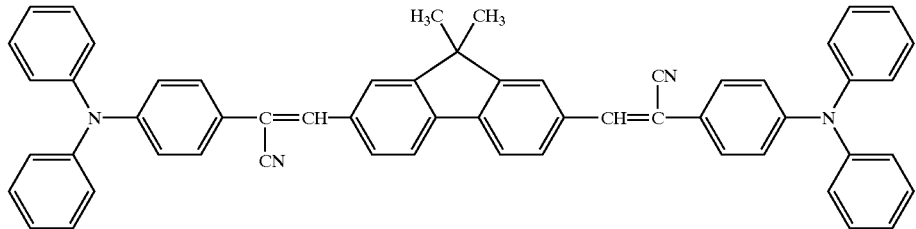

D-5

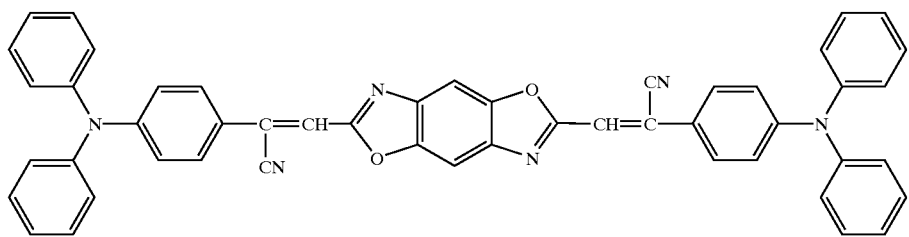
D-6
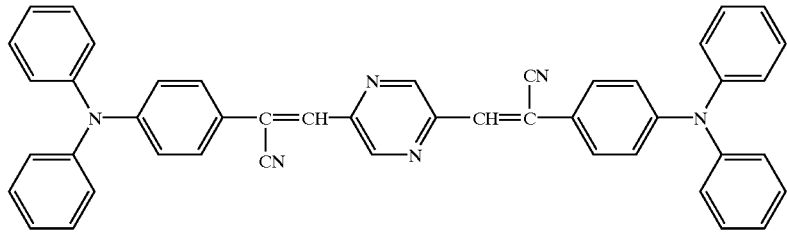
D-7
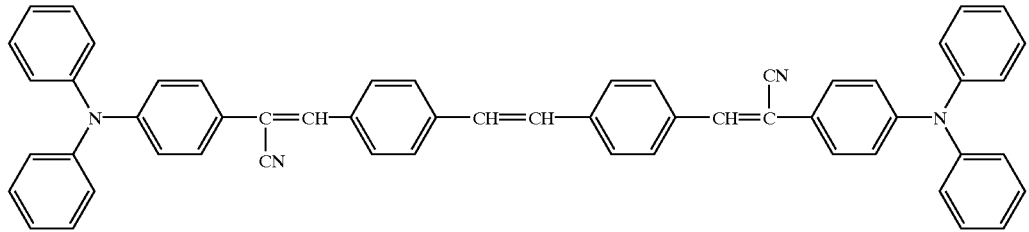
D-8
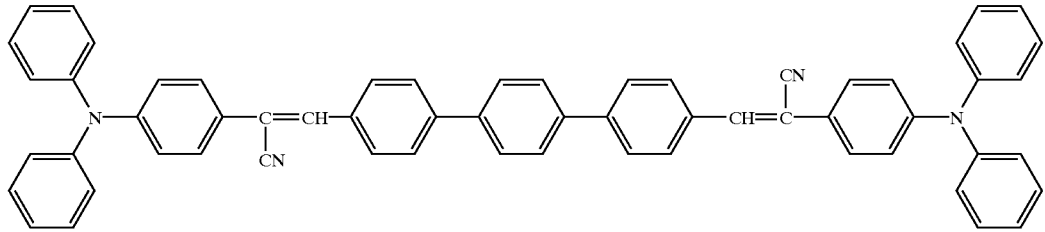
D-9
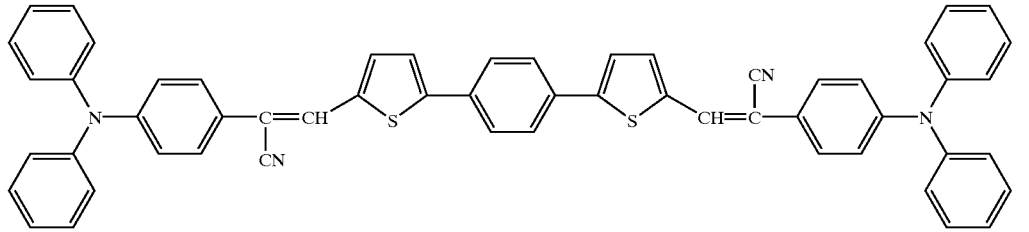
D-10
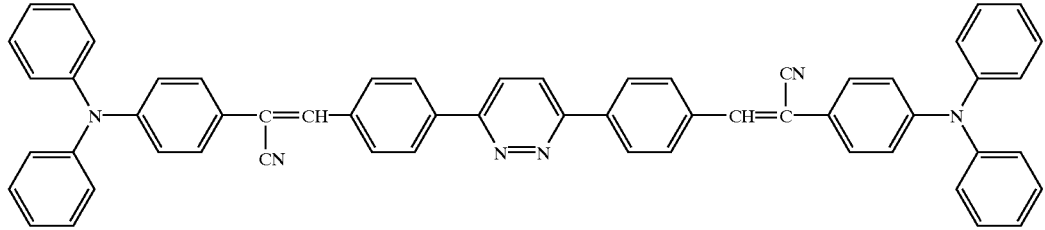
D-11

-continued
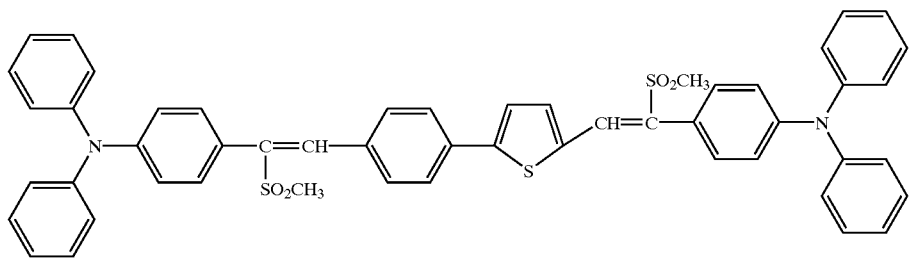
D-12
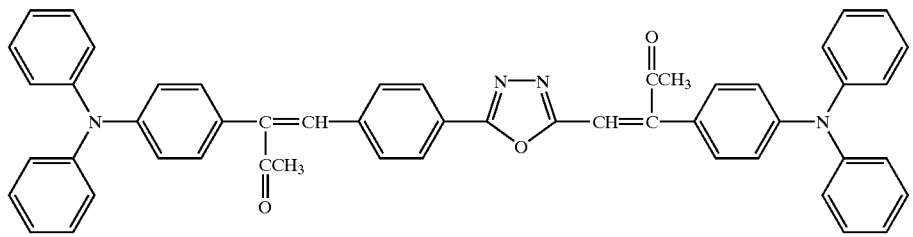
D-13
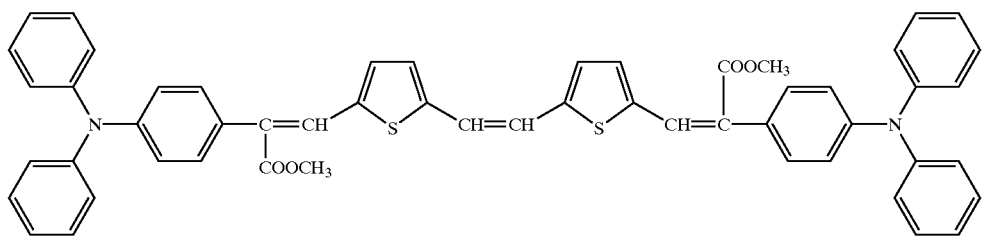
D-14
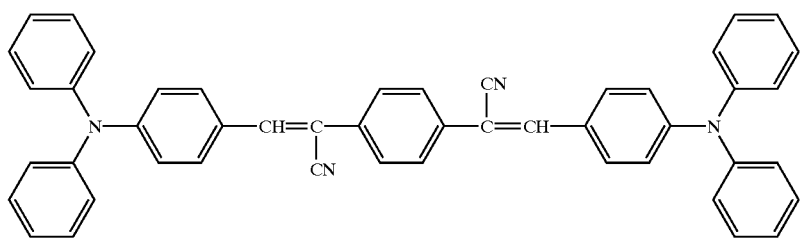
D-15
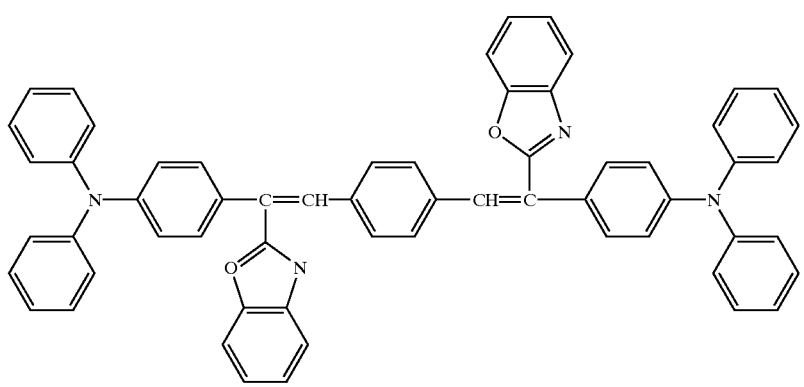
D-16
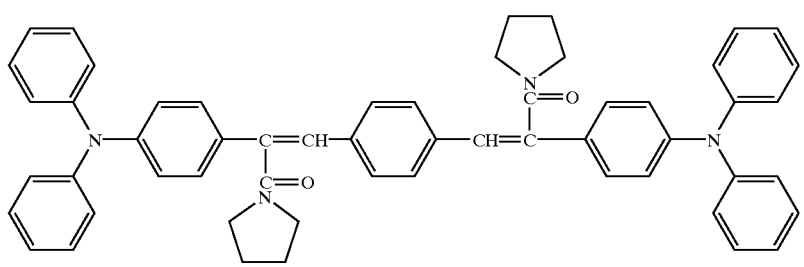
D-17

-continued
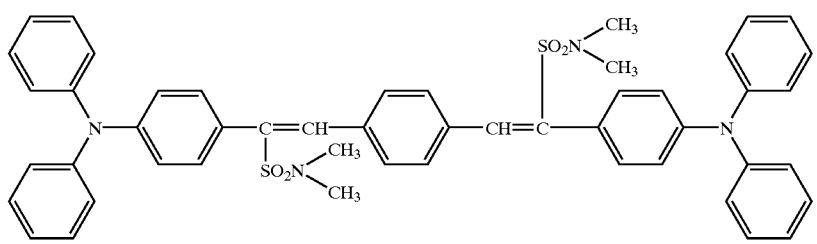
D-18
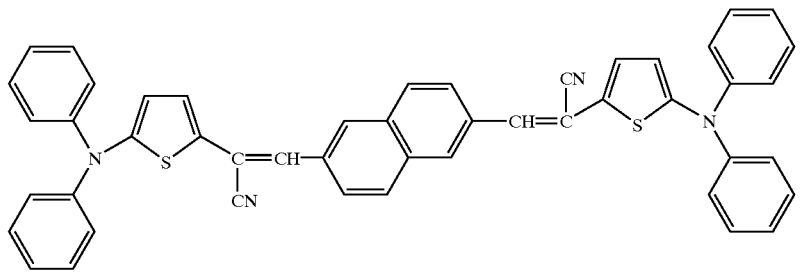
D-19
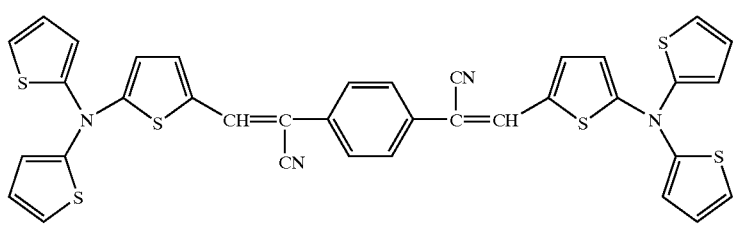
D-20
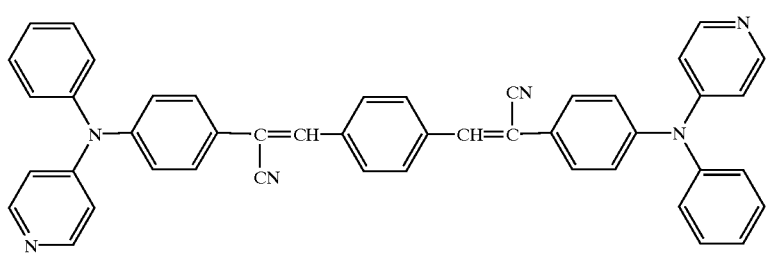
D-21
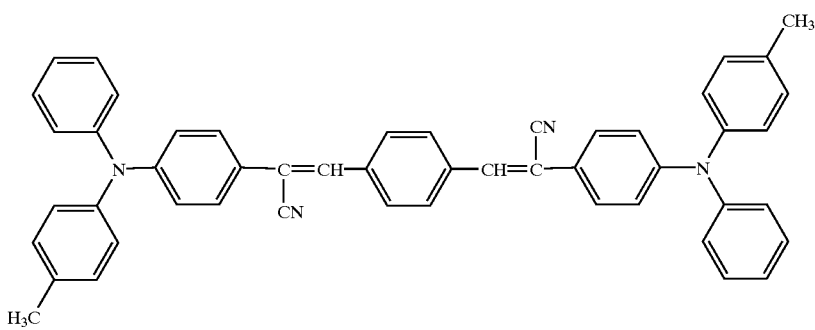
D-22
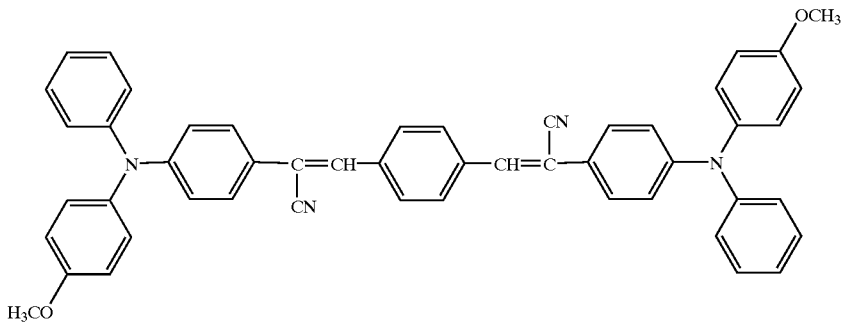
D-23

-continued
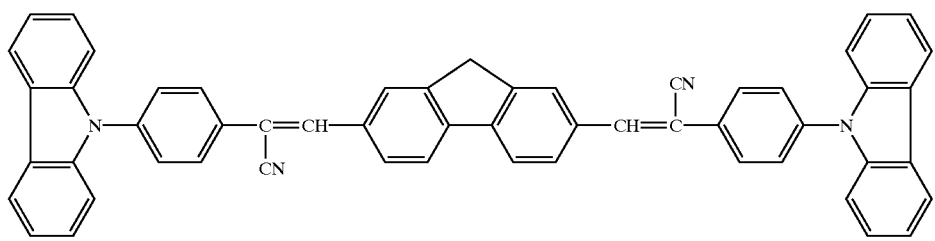
D-24
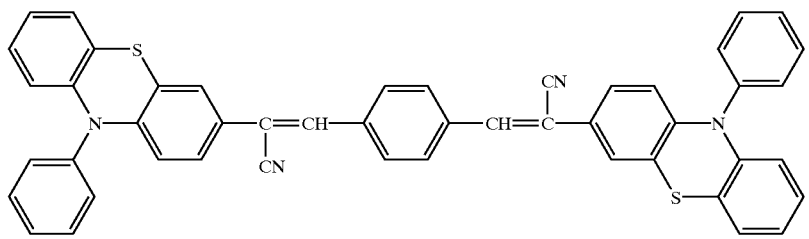
D-25
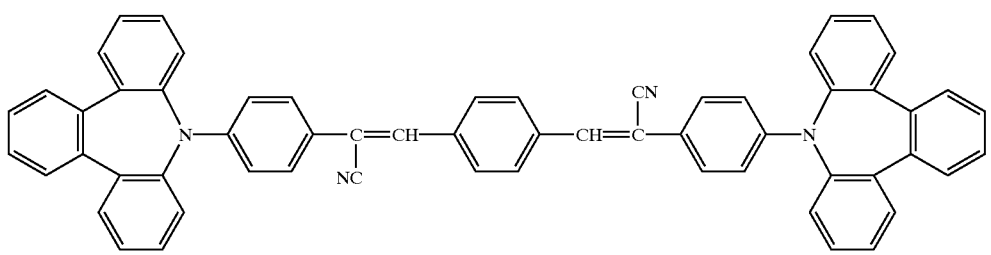
D-26
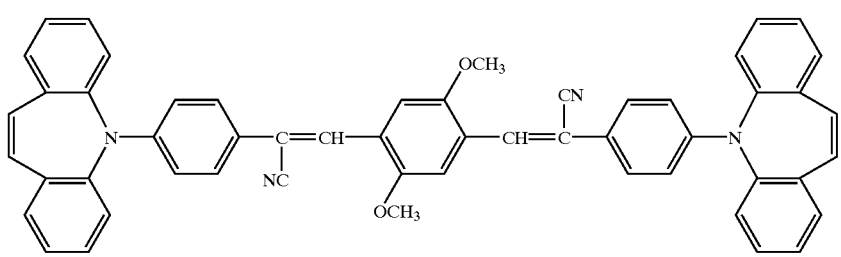
D-27
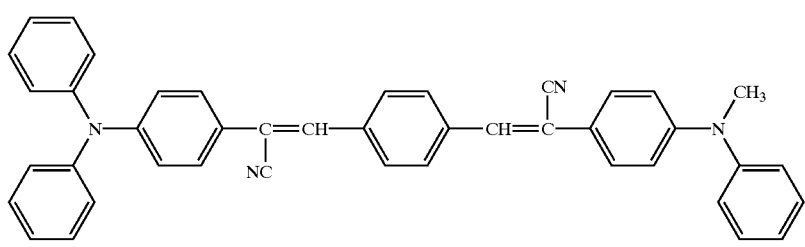
D-28
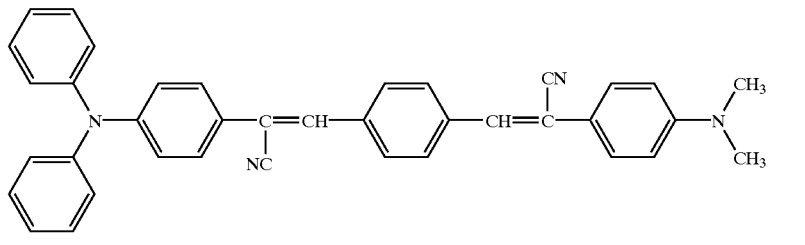
D-29
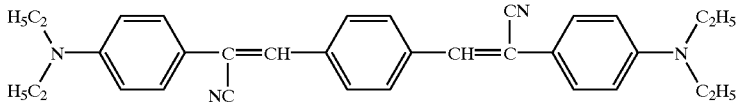
D-30

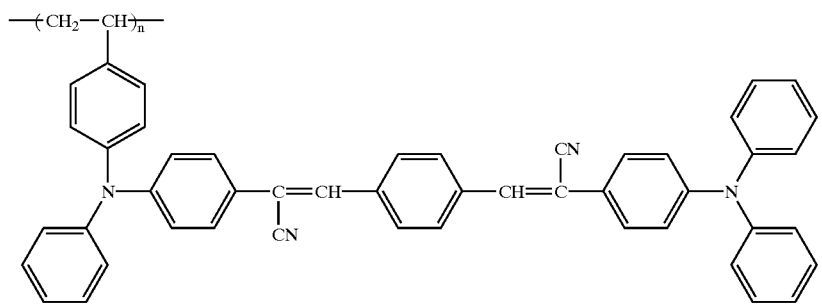
D-31
weight average molecular weight: 60,000 (in terms of polystyrene)
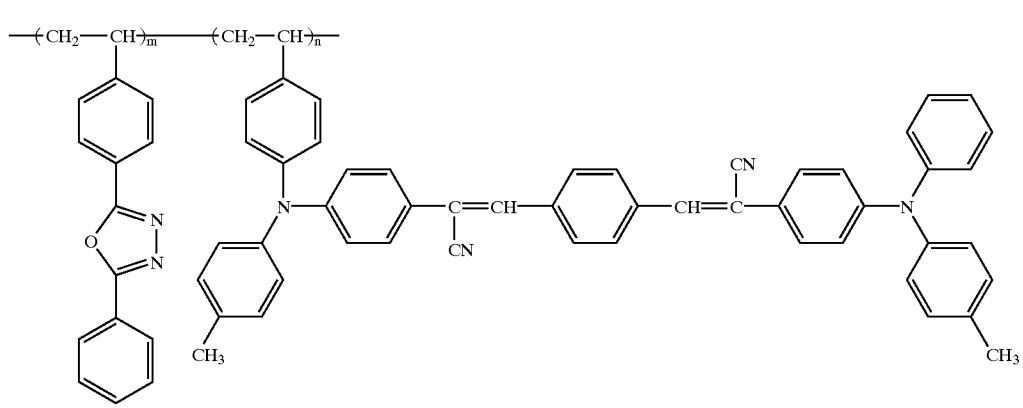
D-32
weight average molecular weight: 20,000 m/n = 1/2 (by weight)
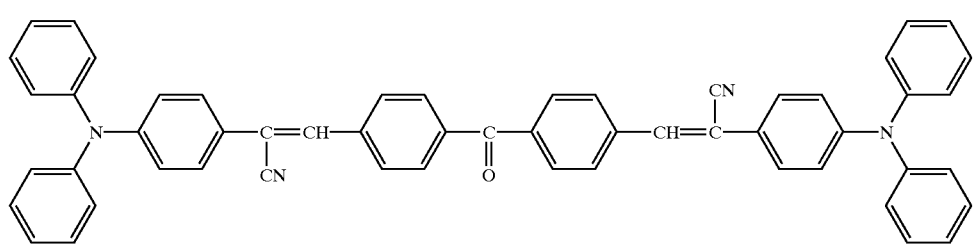
D-33
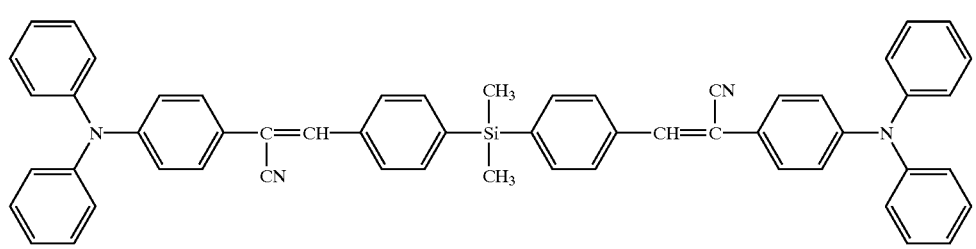
D-34
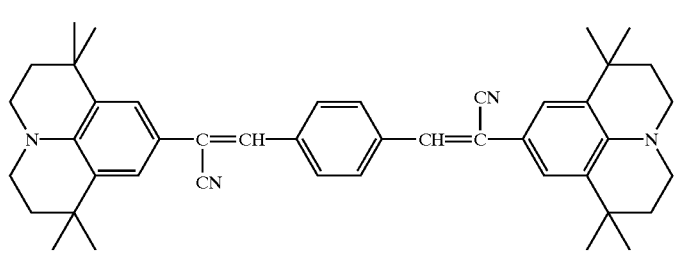
D-35

-continued
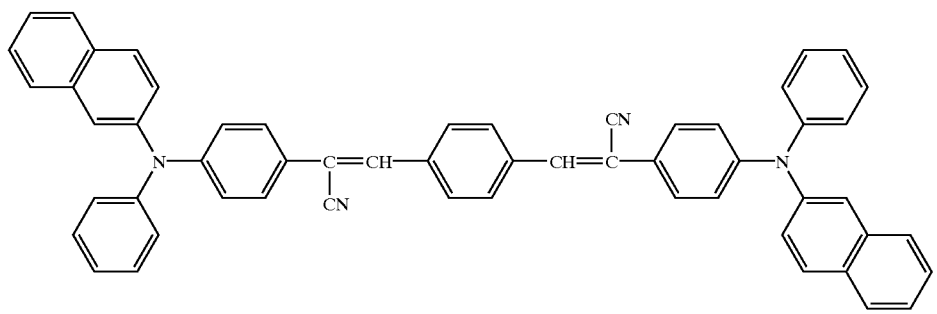
D-36
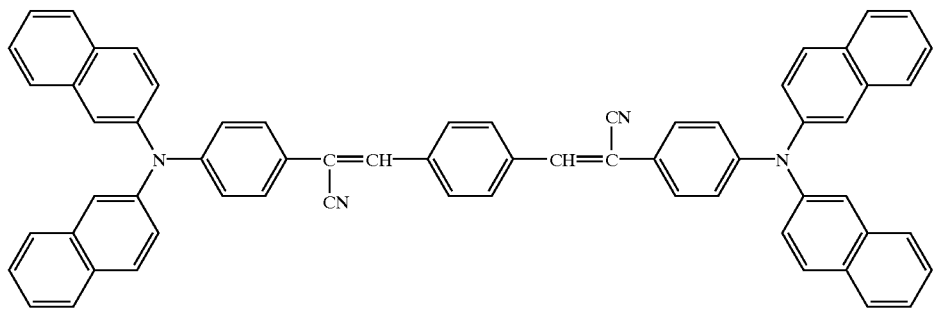
D-37
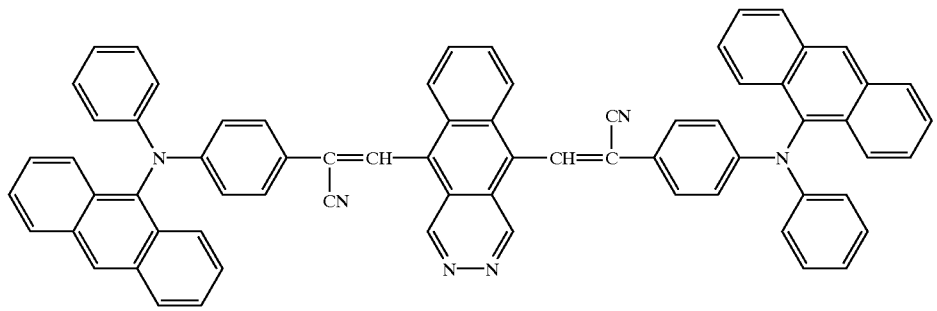
D-38
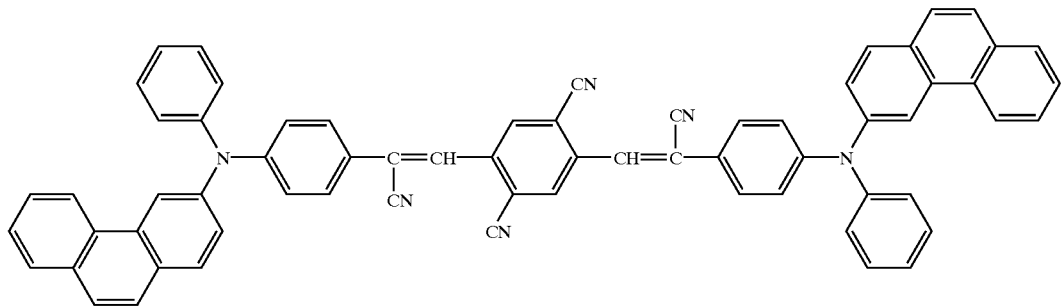
D-39
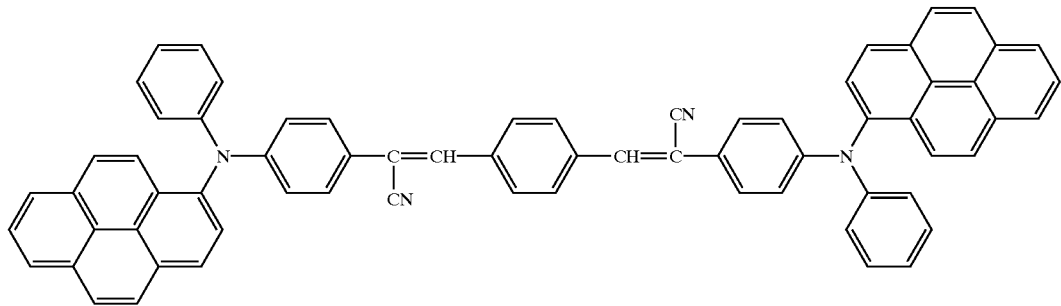
D-40

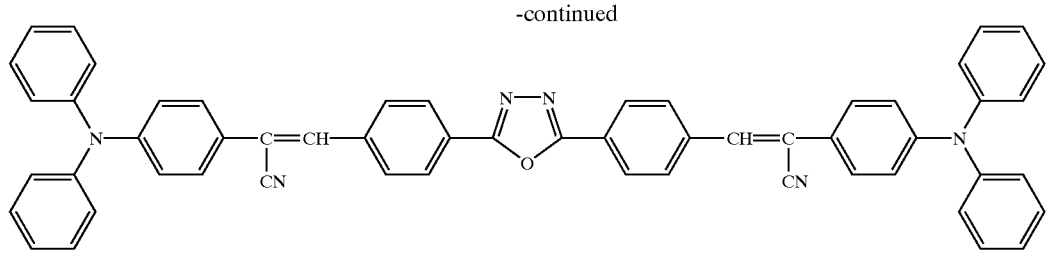
D-41
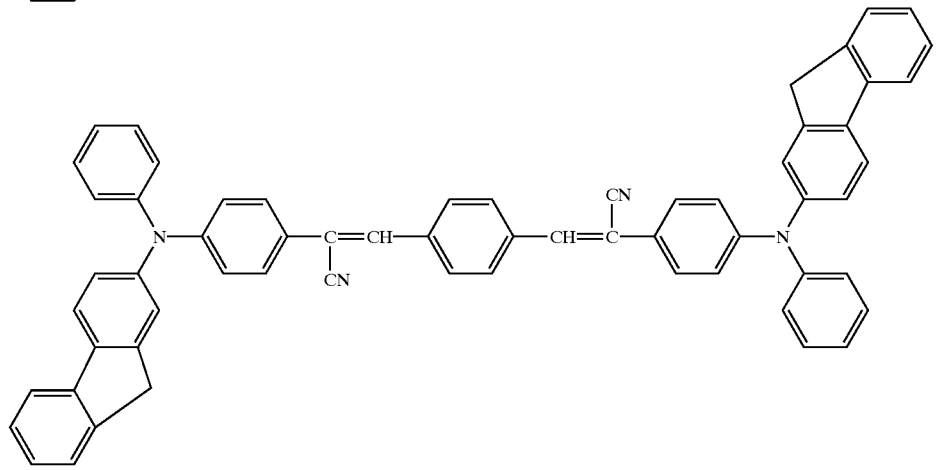
D-42
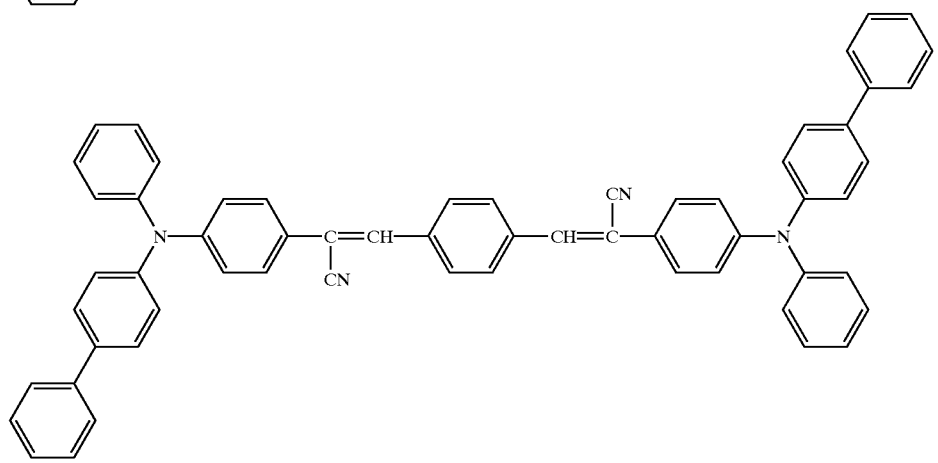
D-43
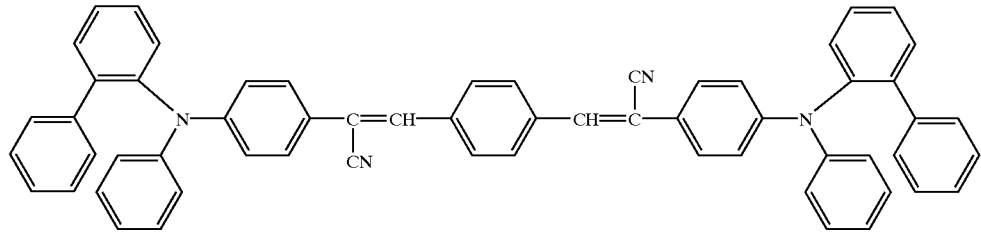
D-44
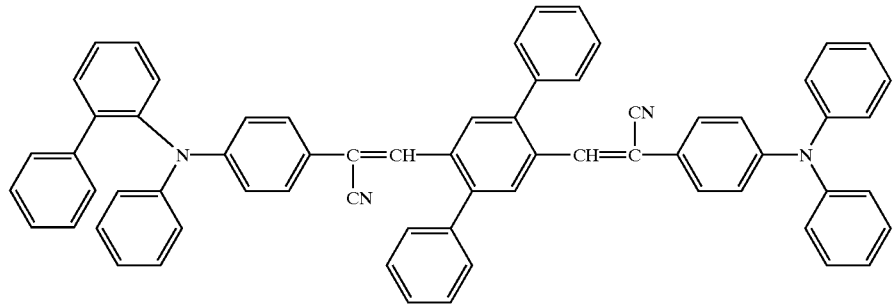
D-45

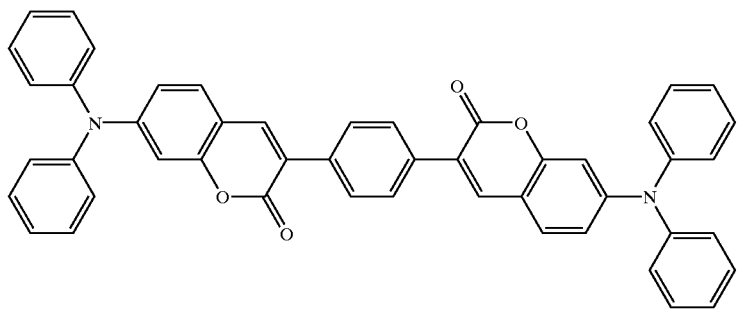
(D-46)
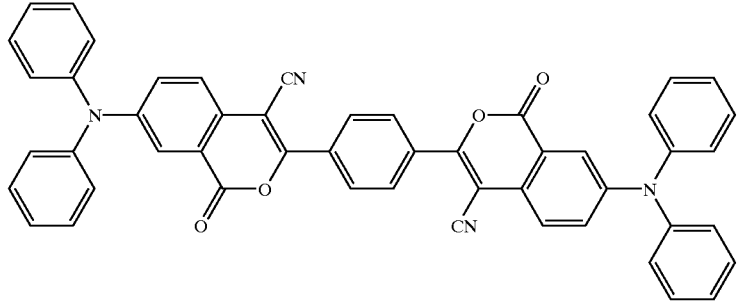
(D-47)
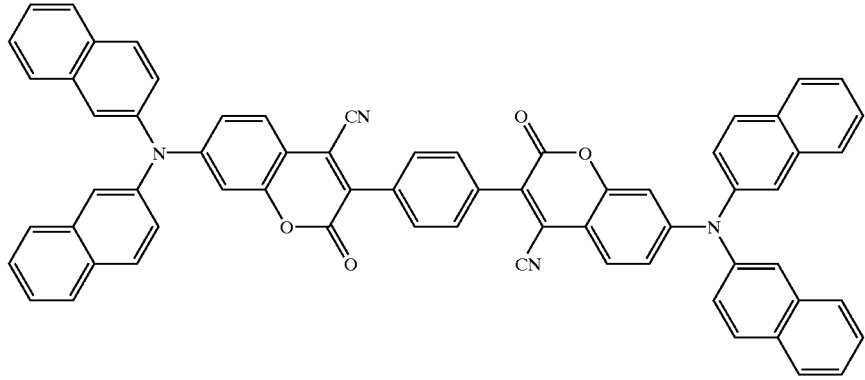
(D-48)
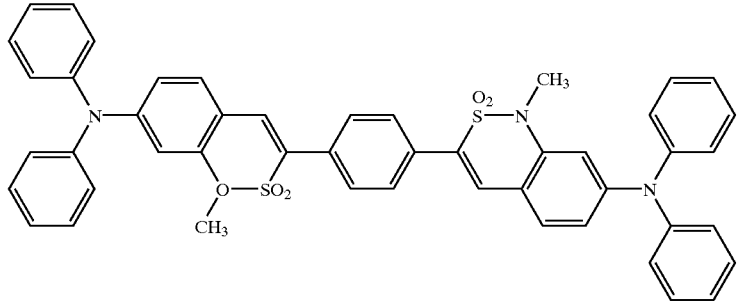
(D-49)
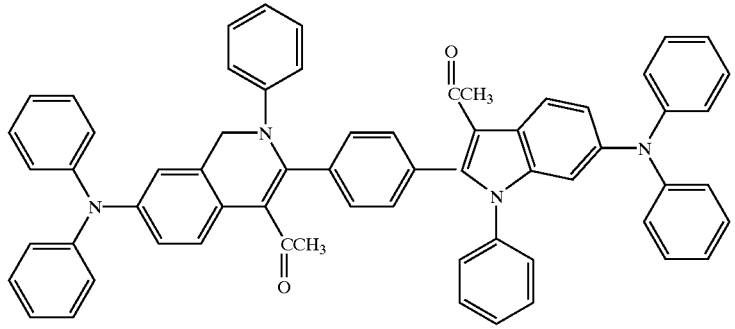
(D-50)

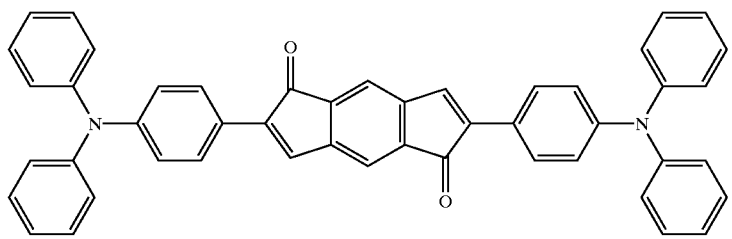

(D-51)

Some synthesis examples of the compounds represented by formula (I) according to the present invention are shown below.

SYNTHESIS EXAMPLE 1

Synthesis of Exemplified Compound (D-1)

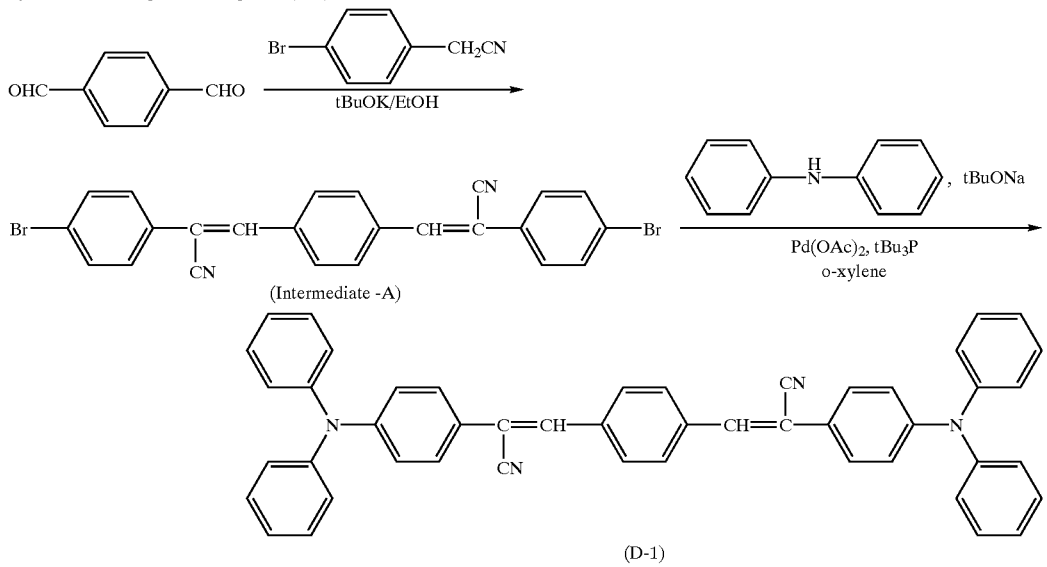

Terephthalaldehyde (1.34 g) and 4.31 g of 4-bromobenzyl cyanide were dissolved in 50 ml of t-butanol, and 2.24 g of potassium t-butoxy was further added thereto and the solution was refluxed for 8 hours with heating. The reaction solution was allowed to be cooled overnight, the crystals precipitated were filtered out and dried, thereby 4.8 g of Intermediate A was obtained. Subsequently, 0.71 g of diphenylamine was dissolved in 15 ml of o-xylene. Under nitrogen atmosphere, 0.46 g of sodium t-butoxy, 0.0224 g of palladium acetate, 0.98 g of Intermediate A, and 0.08 g of t-butylphosphine were added in order to the above-prepared solution and the reaction solution was heated at 105° C. with stirring for 8 hours. After the reaction was finished, ethyl acetate was added to the reaction solution, and the insoluble contents were removed by filtration with sellaite. The thus-obtained ethyl acetate solution was washed with water, dehydrated and concentrated. The crystals obtained were refined with silica gel chromatography. The crystals obtained were recrystallized two times with chloroform-ethyl acetate (1/2), thereby 807 mg of exemplified Compound (D-1) was obtained. (Absorption spectrum λmax=458 nm, in dichloroethane)

SYNTHESIS EXAMPLE 2

Exemplified Compound (D-3) was obtained in an amount of 1.33 g in the same way as in Synthesis Example 1. (Absorption spectrum λmax=476 nm, in dichloroethane)

SYNTHESIS EXAMPLE 3

Exemplified Compound (D-2) was obtained in an amount of 1.50 g in the same way as in Synthesis Example 1. (Absorption spectrum λmax=449 nm, in dichloroethane)

SYNTHESIS EXAMPLE 4

Exemplified Compound (D-36) was obtained in an amount of 1.12 g in the same way as in Synthesis Example 1. (Absorption spectrum λmax=462 nm, in dichloroethane)

SYNTHESIS EXAMPLE 5

Exemplified Compound (D-37) was obtained in an amount of 0.92 g in the same way as in Synthesis Example 1. (Absorption spectrum λmax=464 nm, in dichloroethane)

In the next place, a light emitting device containing the amine compound according to the present invention will be described below. The process of forming the organic layer of a light emitting device containing the amine compound according to the present invention is not particularly limited and, e.g., a resistance heating deposition process, an electron beam process, a sputtering process, a molecular laminating process, a coating process (e.g., a spin coating process, a cast coating process, a dip coating process, etc.), an LB process, an ink jet process and a printing process can be used. A resistance heating deposition process and a coating process are preferably used in view of characteristic aspect and productivity.

A light emitting device according to the present invention comprises a pair of electrodes of the anode and the cathode having formed therebetween a light emitting layer or a plurality of thin layers of organic compound including a luminescent layer, and may comprise a positive hole-injecting layer, a positive hole-transporting layer, an electron-injecting layer, an electron-transporting layer, a protecting layer, etc., in addition to a light emitting layer. Each of these layers may have different functions. Various materials can be used to form each layer.

The anode is to supply positive holes to a positive hole-injecting layer, a positive hole-transporting layer, a light emitting layer, etc., and metals, alloys, metallic oxides, electrically conductive compounds, or mixtures of these compounds can be used therefor, and materials having a work function of 4 eV or more are preferably used. Specific examples of the materials of the anode include electrically conductive metallic oxides such as a tin oxide, a zinc oxide, an indium oxide, an indium tin oxide (ITO), etc., metals such as gold, silver, chromium, nickel, etc., mixtures or laminations of these metals with electrically conductive metallic oxides, inorganic electrically conductive materials such as copper iodide, copper sulfide, etc., organic electrically conductive materials such as polyaniline, polythiophene, polypyrrole, etc., and laminations of these materials with ITO. Electrically conductive metallic oxides are preferably used, and ITO is particularly preferably used in view of producibility, high conductivity and transparency. The layer thickness of the anode can be selected arbitrarily according to materials used but is generally preferably from 10 nm to 5 µm, more preferably from 50 nm to 1 µm, and still more preferably from 100 nm to 500 nm.

The anode generally comprises lamination formed on a soda-lime glass, non-alkali glass or transparent resin substrate. When a glass substrate is used, non-alkali glass is preferably used for lessening elution of ions from the glass. Further, when soda-lime glass is used, it is preferred to provide a barrier coat such as silica. The thickness of the substrate is not particularly limited so long as it can sufficiently stand the mechanical strength. When glass is used, the thickness is generally 0.2 mm or more, preferably 0.7 mm or more. Various processes are used in manufacturing the anode according to the materials to be used. In the case of using ITO, for example, layers are formed by an electron beam process, a sputtering process, a resistance heating deposition process, a chemical reaction process (a sol-gel process), or the process of coating the dispersion of an indium tin oxide. It is possible to reduce the driving voltage or increase the luminous efficacy of the device by the process such as washing of the anode. In the case of using ITO, for instance, UV-ozone processing and plasma processing are effective.

The cathode is to supply electrons to an electron-injecting layer, an electron-transporting layer, a luminescent layer, etc., and the cathode is selected taking into consideration the adhesion with the layers adjacent to the negative electrode such as an electron-injecting layer, an electron-transporting layer, a light emitting layer, etc., ionization potential and stability. As materials of the cathode, metals, alloys, metallic halides, metallic oxides, electrically conductive compounds, or mixtures of these compounds can be used. Specific examples include alkali metals (e.g., Li, Na, K, Cs, etc.) or fluorides of them, alkaline earth metals (e.g., Mg, Ca, etc.) or fluorides of them, gold, silver, lead, aluminum, sodium-potassium alloys or mixed metals of them, lithium-aluminum alloys or mixed metals of them, magnesium-silver alloys or mixed metals of them, and rare earth metals such as indium, ytterbium, etc., preferably materials having a work function of 4 eV or less, and more preferably aluminum, lithium-aluminum alloys or mixed metals of them, and magnesium-silver alloys or mixed metals of them. The cathode can take not only the monolayer structures of the above compounds and mixtures thereof but also the laminating structures including the above compounds and mixtures thereof. The layer thickness of the cathode can be selected arbitrarily according to the materials used but is generally preferably from 10 nm to 5 µm, more preferably from 50 nm to 1 µm, and still more preferably from 100 nm to 1 µm. Processes such as an electron beam process, a sputtering process, a resistance heating deposition process, and a coating process are used in the manufacture of the cathode, and a single metal can be vapor deposited or two or more components can be deposited at the same time. Further, a plurality of metals can be deposited at the same time to form an alloy electrode, alternatively a previously prepared alloy can be deposited. It is preferred that the sheet resistance of the anode and the cathode be low, preferably several hundred ω/□ or less.

The light emitting layer may be formed of any material so long as, when electric field is impressed, the light emitting layer formed does not prevent positive holes from being injected from the anode, or the positive hole-injecting layer and the positive hole-transporting layer, electrons from being injected from the cathode, or the electron-injecting layer and the electron-transporting layer, and offers the functions of transferring the electric charge injected and recombining the electrons and positive holes to effect emission. Preferably the light emitting layer contains the amine compound according to the present invention but other light emitting materials can also be used, e.g., benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perynone derivatives, oxadiazole derivatives, aldazine derivatives, pyrralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, aromatic dimethylidyne compounds, various metal complexes such as transition metal complexs belonging to group VIII represented by metal complexes of 8-quinolinol derivatives, rare earth metal complexes, and Ir, Ru and Pt, and polymer compounds such as polythiophene, polyphenylene, and polyphenylene vinylene are exemplified. The layer thickness of the light emitting layer is not particularly restricted but it is generally preferably from 1 nm to 5 µm, more preferably from 5 nm to 1 µm, and still more preferably from 10 nm to 500 nm.

The light emitting layer can be formed by any process, e.g., a resistance heating deposition process, an electron beam process, a sputtering process, a molecular laminating process, a coating process (a spin coating process, a cast coating process, a dip coating process), an LB process, an ink jet process or a printing process is used, preferably a resistance heating deposition process and a coating process.

Materials of the positive hole-injecting layer and the positive hole-transporting layer are sufficient if they have any of the functions of injecting positive holes from the anode, transporting positive holes, and barriering off the electrons injected from the cathode. Specific examples of the materials include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, aniline-based copolymers, and electrically conductive high molecular weight oligomers such as tihophene oligomers and polythiophene. The layer thickness of the positive hole-injecting layer and the positive hole-transporting layer is not particularly limited but the thickness is generally preferably from 1 nm to 5 μm, more preferably from 5 nm to 1 μm, and still more preferably from 10 nm to 500 nm. The positive hole-injecting layer and the positive hole-transporting layer may be monolayer structures comprising one or two or more of the above materials, or may be multilayer structures comprising a plurality of layers of the same compositions or different compositions.

The positive hole-injecting layer and the positive hole-transporting layer are formed by a vacuum deposition process, an LB process, an ink jet process, a printing process, or a process of dissolving or dispersing the above-described positive hole-injecting and transporting agent in a solvent and coating (a spin coating process, a cast coating process, a dip coating process, etc.). In the case a coating process, a positive hole-injecting and transporting agent can be dissolved or dispersed with a resin component. Examples of such resin components include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, etc.

Materials of the electron-injecting layer and the electron-transporting layer are sufficient if they have any of the functions of injecting electrons from the cathode, transporting electrons, and barriering off the positive holes injected from the anode. Specific examples of the materials include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbidimide derivatives, fluorenylidene methane derivatives, distyrylpyrazine derivatives, tetracarboxylic acid anhydrides of aromatic condensed rings such as naphthalene and perylene, phthalocyanine derivatives, and various metal complexes represented by metal complexes such as metal complexes of 8-quinolinol derivatives and metal complexes having a ligand such as metal phthalocyanine, benzoxazole or benzothiazole. The layer thickness of the electron-injecting layer and the electron-transporting layer is not particularly restricted but the thickness is generally preferably from 1 nm to 5 μm, more preferably from 5 nm to 1 μm, and still more preferably from 10 nm to 500 nm. The electron-injecting layer and the electron-transporting layer may be monolayer structures comprising one or two or more of the above materials, or may be multilayer structures comprising a plurality of layers of the same compositions or different compositions.

The electron-injecting layer and the electron-transporting layer are formed by a vacuum deposition process, an LB process, an ink jet process, a printing process, or a process of dissolving or dispersing the above-described electron-injecting and transporting agent in a solvent and coating (a spin coating process, a cast coating process, a dip coating process, etc.). In the case a coating process, an electron-injecting and transporting agent can be dissolved or dispersed with a resin component. As the resin components, those exemplified in the positive hole-injecting and transporting layers can be applied.

Materials of the protective layer are sufficient if they have the function of preventing substances which accelerates the deterioration of the device, such as water and oxygen, from entering the device. Specific examples of such materials include metals, e.g., In, Sn, Pb, Au, Cu, Ag, Al, Ti, Ni, etc., metallic oxides, e.g., MgO, SiO, $SiO_2$, $Al_2O_3$, GeO, NiO, CaO, BaO, $Fe_2O_3$, $Y_2O_3$, $TiO_2$, etc., metallic fluorides, e.g., $MgF_2$, LiF, $AlF_3$, $CaF_2$, etc., polyethylene, polypropylene, polymethyl methacrylate, polyimide, polyurea, polytetrafluoroethylene, polychlorotrifluoroethylene, polydichlorodifluoroethylene, copolymers of chlorotrifluoroethylene and dichlorodifluoroethylene, copolymers obtained by copolymerizing tetrafluoroethylene with monomer mixtures containing at least one comonomer, fluorine-containing copolymers having cyclic structure at the main chain of the copolymer, water-absorbing substances having a water absorption coefficient of 1% or more, and moisture-proof materials having a water absorption coefficient of 0.1% or less.

The forming process of the protective layer is also not particularly restricted and, e.g., a vacuum deposition process, a sputtering process, a reactive sputtering process, an MBE (molecular beam epitaxy) process, a cluster ion beam process, an ion-plating process, a plasma polymerization process (a high frequency exciting ion-plating process), a plasma CVD process, a laser CVD process, a heat CVD process, a gas source CVD process, a coating process, or an ink jet process can be applied.

The present invention will be specifically described below with referring to examples, but it should not be construed as the present invention is limited thereto.

EXAMPLE 1

A transparent supporting substrate comprising a glass substrate of a size of 25 mm×25 mm×0.7 mm having coated thereon ITO in a thickness of 150 nm (manufactured by Tokyo Sanyo Shinku Co., Ltd.) was used. After this transparent supporting substrate was subjected to etching and washing, copper phthalocyanine was deposited in a thickness of about 10 nm. Then, TPD (N,N'-bis(3-methylphenyl)-N,N'-diphenylbenzidine) in a thickness of about 40 nm, the compound shown in Table 1 below in a thickness of about 40 nm, and Alq (tris(8-hydroxyquinolinato)aluminum) (as the fourth layer) in a thickness of about 20 nm were vapor deposited in order in vacuo of $10^{-3}$ to $10^{-4}$ Torr under the substrate temperature condition of room temperature. A mask which had been subjected to patterning (a mask having a light emitting area of 5 mm×5 mm) was set up on the organic thin layer, and magnesium/silver in the ratio of 10/1 were co-deposited in a thickness of 250 nm in a depositing apparatus, then silver was deposited in a thickness of 300 nm, thereby a luminescence device was prepared.

Direct current constant voltage was impressed to the EL device to effect emission using source measuring unit model 2400 (manufactured by Toyo Technica Co., Ltd.). The luminance was measured with luminescence meter BM-8 (manufactured by Topcon Co., Ltd.), and the emission wavelength was measured using spectrum analyzer PMA-11 (manufactured by Hamamatsu Photonics Co., Ltd.). The results obtained are shown in Table 1 below.

An device was manufactured using Compound ET-1 in place of Alq and evaluation was performed.

TABLE 1

| Compound | Compound of the Fourth Layer | Maximum Luminance (cd/m$^2$) | Driving Voltage (V) | CIE Chromaticity Coordinates (x, y) | Generation of Dark Spots (after 100 hr. emission) |
|---|---|---|---|---|---|
| Comparative Compound A | Alq | 3,000 | 13 | (0.25, 0.35) | Δ |
| Comparative Compound B | Alq | 2,000 | 13 | (0.35, 0.56) | x |
| Exemplified Compound D-1 | Alq | 3,400 | 13 | (0.57, 0.42) | o |
| Exemplified Compound D-3 | Alq | 4,000 | 12 | (0.56, 0.43) | o |
| Exemplified Compound D-5 | Alq | 4,500 | 13 | (0.62, 0.37) | o |
| Exemplified Compound D-1 | ET-1 | 6,000 | 15 | (0.57, 0.41) | o | o: Dark spots were not observed visually.
Δ: Dark spots were observed a little.
x: Dark spots were observed very much.

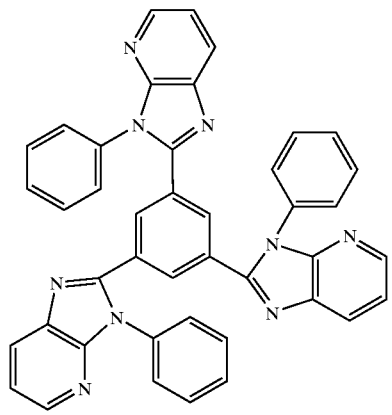

ET-1

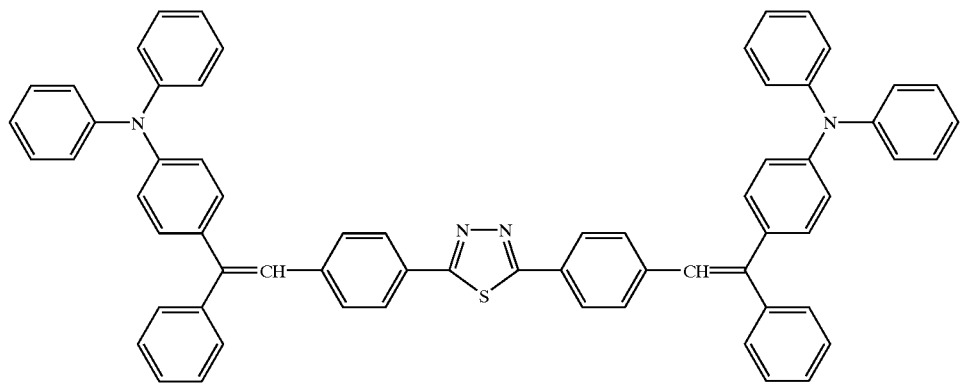

Comparative Compound A (Compound disclosed in JP-A-10-152677, (the term "JP-A" as used herein means an "unexamined published Japanese patent application"))

Comparative Compound B

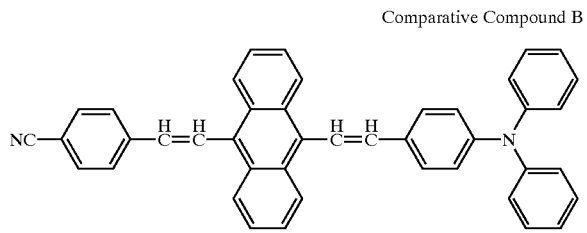

As is apparent from the results in Table 1, the compounds according to the present invention can emit orange to red colors with high luminance when used alone in the light emitting layer as against green-blue luminescence of comparative compounds. It is also confirmed that the compounds according to the present invention can be used as light emitting materials having high durability. Further, the compound of the present invention is capable of emission with higher luminance when used in combination with Compound ET-1.

EXAMPLE 2

After ITO substrate was subjected to etching and washing in the same manner as in Example 1, TPD was deposited in a thickness of about 40 nm, and then the compound shown in Table 2 below and Alq (tris(8-hydroxyquinolinato) aluminum) were co-deposited at depositing rate of 0.004 nm/sec and 0.4 nm/sec, respectively, in a layer thickness of about 40 nm. Further, Alq was deposited alone in a thickness of 20 nm. Subsequently, deposition of the cathode was performed in the same manner as in Example 1 to prepare a light emitting device and evaluation was performed. The results obtained are shown in Table 2 below.

TABLE 2

| Compound | Maximum Luminance (cd/m$^2$) | Driving Voltage (V) | Emission Wavelength λmax (nm) | CIE Chromaticity Coordinates (x, y) | Generation of Dark Spots (after 100 hr. emission) |
|---|---|---|---|---|---|
| Exemplified Compound D-1 | 2,500 | 16 | 600 | (0.53, 0.46) | ○ |
| Exemplified Compound D-3 | 4,800 | 16 | 615 | (0.60, 0.40) | ○ |
| Exemplified Compound D-5 | 3,000 | 16 | 625 | (0.62, 0.39) | ○ |

The results in Table 2 show that when the compounds according to the present invention are used as light emitting materials for doping, light emitting devices exhibiting high luminance emission and high durability can be obtained.

EXAMPLE 3

After ITO substrate was subjected to etching and washing in the same manner as in Example 1, 40 mg of poly(N-vinylcarbazole), 12 mg of PBD (2-(4-biphenylyl)-5-(4-tert-butylphenyl)-1,3,4-oxadiazole), and 0.5 mg of the compound described in Table 1 were dissolved in 3 ml of 1,2-dichloroethane and the solution was spin-coated on the above-washed ITO substrate. The layer thickness of the thus-formed organic thin layer was about 100 nm. Deposition of the cathode was subsequently performed in the same manner as in Example 1 to prepare a light emitting device and evaluation was performed. The results obtained are shown in Table 3 below.

TABLE 3

| Compound | Maximum Luminance (cd/m$^2$) | Driving Voltage (V) | Emission Wavelength λmax (nm) | CIE Chromaticity Coordinates (x, y) |
|---|---|---|---|---|
| Exemplified Compound D-1 | 500 | 16 | 601 | (0.56, 0.42) |
| Exemplified Compound D-3 | 700 | 16 | 612 | (0.59, 0.41) |
| Exemplified Compound D-5 | 400 | 17 | 620 | (0.60, 0.40) |

It can be apparently seen from the results in Table 3 that, as compared with the comparative sample, the device in which the compound of the present invention is used is capable of high luminance emission with low driving voltage even in a coating process, where emission luminance is generally low.

EXAMPLE 4

After ITO substrate was subjected to etching and washing in the same manner as in Example 1, Exemplified Compound D-1 was deposited in a thickness of about 60 nm, successively Alq was deposited in a thickness of about 40 nm. Thereafter, deposition of the cathode was performed in the same manner as in Example 1 to prepare a light emitting device and evaluation was carried out.

As a result of evaluation, luminance of the device at driving voltage of 15 V was 2,500 cd/m$^2$. High luminance emission of λmax=602 nm, and CIE chromaticity coordinates (x, y)=(0.57, 0.41) was observed, which confirmed that the compound according to the present invention was effective as a combination positive hole-injecting/transporting agent and light emitting agent.

EXAMPLE 5

On an ITO glass substrate subjected to etching and washing in the same manner as in Example 1 were deposited NPD (N,N'-bis(1-naphthyl)-N,N'-diphenylbenzidine) in a thickness of about 40 nm, exemplified Compound D-2 in a thickness of about 20 nm, Bathocuproine in a thickness of about 10 nm, and Alq (tris(8-hydroxyquinolinato) aluminum) in a thickness of about 30 nm. Subsequently, deposition of the cathode was performed in the same manner as in Example 1 to prepare a light emitting device and evaluation was performed. The device showed high luminance emission of 3,500 cd/m$^2$ at driving voltage of 16 V.

EXAMPLE 6

The solution obtained by dissolving 40 mg of poly(N-vinylcarbazole), 12 mg of 2,5-bis(1-naphthyl)-1,3,4- oxadiazole, 10 mg of 1,1,4,4-tetraphenylbutadiene, and 0.1 mg of exemplified Compound D-1 in 3 ml of 1,2-dichloroethane was spin-coated on an ITO glass substrate which had been subjected to etching and washing in the same manner as in Example 1. The thickness of the organic layer was about 120 nm. Subsequently, deposition of the cathode was performed in the same manner as in Example 1 to prepare a light emitting device. Direct current voltage was impressed to this device with ITO electrode as the anode and Mg/Ag electrode as the cathode and luminous characteristics were examined. White luminescence (luminance: 2,200 cd/m$^2$) on CIE chromaticity coordinates (x, y) of (0.36, 0.35) at driving voltage of 15 V was obtained, which confirmed that the compound according to the present invention was effective for white luminescence.

EFFECT OF THE INVENTION

The organic light emitting device containing the triarylamine compound according to the present invention is capable of high luminance emission. In particular, the non-doping type device (a device having a light emitting layer comprising a single dye), where high luminance emission has been thought to be difficult, has realized high luminance emission with high durability. Thus the manufacture of the device showing less unevenness in performance among devices and advantageous in the production cost as compared with a doping type device has been realized according to the present invention. Further, good luminescent (light emitting) characteristics can be obtained even in a coating system where emission luminance is in general low.

While the invention has been described in detail and with reference to specific examples thereof, it will be apparent to one skilled in the art that various changes and modifications can be made therein without departing from the spirit and scope thereof.

What is claimed is:

1. An organic electroluminescent device comprising a pair of electrodes and at least one organic thin layer comprising a light emitting layer between the electrodes, wherein the organic electroluminescent device emits electroluminescence when an electric field is applied across the electrodes wherein electrons and positive holes recombine to produce light in the light emitting layer, and wherein the at least one organic thin layer contains at least one compound represented by the following formula (I), and the at least one compound represented by the following formula (I) emits fluorescence when an electric field is applied across the electrodes:

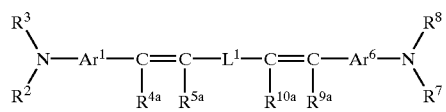

wherein $Ar^1$ and $Ar^6$, which are the same or different, each represents a divalent aryl group or a divalent heterocyclic group; $R^2$, $R^3$, $R^7$ and $R^8$, which are the same or different, each represents an aryl group, a heterocyclic group or an aliphatic hydrocarbon group; $Ar^1$, $R^2$ and $R^3$, and $Ar^6$, $R^7$ and $R^8$ may be linked to form a ring; $R^{4a}$, $R^{5a}$, $R^{9a}$ and $R^{10a}$, which are the same or different, each represents a hydrogen atom or a monovalent group, and at least one of $R^{4a}$, $R^{5a}$, $R^{9a}$ and $R^{10a}$ represents an electron withdrawing group having a Hammett's $\sigma_p$ value of 0.2 or more; $L^1$ represents (i) a divalent monocyclic or bicyclic aryl group, or a divalent monocyclic or bicyclic aryl group to which a heterocyclic ring is condensed, (ii) a divalent heterocyclic group, or (iii) a divalent group comprising one of two divalent aryl groups, two divalent heterocyclic groups, and a divalent aryl group and a divalent heterocyclic group, which groups are each connected by a single bond, a vinyl group, a C=X group, a silyl group, an aryl group, a 6-membered aromatic heterocyclic group, a 5-membered aromatic heterocyclic group comprising a carbon atom, a nitrogen atom and an oxygen atom, or the combination of these groups; X represents an oxygen atom, a sulfur atom, N—$R^{x1}$ or $CR^{x2}R^{x3}$; and $R^{x1}$, $R^{x2}$ and $R^{x3}$, which are the same or different, each represents a hydrogen atom or a substituent.

2. An organic electroluminescent device of claim 1, wherein the organic electroluminescent device comprises at least one compound represented by formula (I) dispersed in a polymer.

3. The organic electroluminescent device of claim 1, wherein the compound represented by formula (I) is a compound represented by the following formula (II):

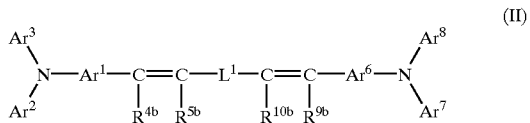

wherein $Ar^1$, $Ar^6$ and $L^1$ each has the same meaning as in formula (I); $Ar^2$, $Ar^3$, $Ar^7$ and $Ar^8$, which are the same or different, each represents an aryl group or a heterocyclic group; and $R^{4b}$, $R^{5b}$, $R^{9b}$ and $R^{10b}$, which are the same or different, each represents a hydrogen atom, a heterocyclic group, a perhalogenoalkyl group, a cyano group, an oxycarbonyl group, a carbamoyl group, a sulfonyl group, a sulfamoyl group, or an acyl group, provided that all of $R^{4b}$, $R^{5b}$, $R^{9b}$ and $R^{10b}$ do not represent hydrogen atoms at the same time.

4. An organic electroluminescent device of claim 3, wherein the organic electroluminescent device comprises at least one compound represented by formula (II) dispersed in a polymer.

5. The organic electroluminescent device of claim 3, wherein the compound represented by formula (II) is a compound represented by the following formula (III):

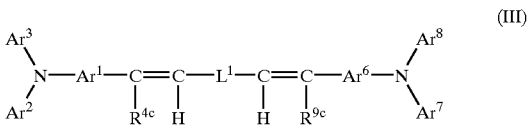

wherein $Ar^1$, $Ar^2$, $Ar^3$, $Ar^6$, $Ar^7$, $Ar^8$ and $L^1$ each has the same meaning as in formula (II); $Ar^1$, $Ar^2$ and $Ar^3$, and $Ar^6$, $Ar^7$ and $Ar^8$ may be linked to form a ring; and $R^{4c}$ and $R^{9c}$, which are the same or different, each represents a heterocyclic group, a perhalogenoalkyl group, a cyano group, an oxycarbonyl group, a carbamoyl group, a sulfonyl group, a sulfamoyl group, or an acyl group.

6. An organic electroluminescent device of claim 5, wherein the organic electroluminescent device comprises at least one compound represented by formula (III) dispersed in a polymer.

7. An organic electroluminescent device of claim 1, wherein the at least one organic thin layer contains at least one compound represented by the formula (I) and an electron-transporting material.

8. An organic electroluminescent device of claim 1, wherein the at least one organic thin layer comprising the organic thin layer contains at least one compound represented by the formula (I) and an electron-transporting layer.

* * * * *